US010048243B2

(12) United States Patent
Yamamoto

(10) Patent No.: US 10,048,243 B2
(45) Date of Patent: Aug. 14, 2018

(54) AUTOMATIC WATER QUALITY SURVEILLANCE APPARATUS

(71) Applicants: KANKYO ELECTRONICS CO., LTD, Fukuoka (JP); Takahiro Yamamoto, Fukuoka (JP)

(72) Inventor: Takahiro Yamamoto, Fukuoka (JP)

(73) Assignees: KANKYO ELECTRONICS CO., LTD, Fukuoka (JP); Takahiro Yamamoto, Fukuoka (JP)

( * ) Notice: Subject to any disclaimer, the term of this patent is extended or adjusted under 35 U.S.C. 154(b) by 0 days.

(21) Appl. No.: 15/699,753

(22) Filed: Sep. 8, 2017

(65) Prior Publication Data

US 2018/0074035 A1   Mar. 15, 2018

(30) Foreign Application Priority Data

Sep. 14, 2016   (JP) .................................. 2016-179079

(51) Int. Cl.
| | | |
|---|---|---|
| *G01N 33/18* | (2006.01) | |
| *G01N 27/12* | (2006.01) | |
| *C12Q 1/04* | (2006.01) | |
| *H04N 7/18* | (2006.01) | |
| *G08B 21/18* | (2006.01) | |
| *A01K 63/04* | (2006.01) | |

(Continued)

(52) U.S. Cl.
CPC ........... *G01N 33/186* (2013.01); *A01K 61/10* (2017.01); *A01K 63/04* (2013.01); *A01K 63/065* (2013.01); *C12Q 1/04* (2013.01); *G01N 27/125* (2013.01); *G06T 7/0004* (2013.01); *G08B 21/18* (2013.01); *H04N 7/183* (2013.01); *C12Q 2304/40* (2013.01); *G06T 2207/10016* (2013.01); *G06T 2207/30108* (2013.01)

(58) Field of Classification Search
CPC ...... A01K 61/10; A01K 63/04; A01K 63/065; C12Q 1/04; C12Q 2304/40; G01N 27/125; G01N 33/186; G06T 7/0004; G06T 2207/10016; G06T 2207/30108; G08B 21/18; H04N 7/183
See application file for complete search history.

(56) References Cited

U.S. PATENT DOCUMENTS

2014/0277746 A1*  9/2014  Konishi .................. C02F 1/008
                                                  700/265
2017/0325427 A1*  11/2017  Straight ............... A01K 63/045

FOREIGN PATENT DOCUMENTS

| JP | S62-299751 A | 12/1987 |
|---|---|---|
| JP | H04-083575 A | 3/1992 |

(Continued)

OTHER PUBLICATIONS

Office Action dated Oct. 4, 2016, issued in Japanese Patent Application No. 2016-179079, with translation (8 pages).

*Primary Examiner* — Edward Park
(74) *Attorney, Agent, or Firm* — Nakanishi IP Associates, LLC

(57) ABSTRACT

Provided is a small and simple automatic water quality surveillance apparatus that can automatically sense toxic substances, oil, mold, or the like contained in raw water. The apparatus includes an odor-sensing water tank through which the raw water circulates. The tank further includes an odor sensor sensing an odor, such as an oily odor, a mold odor, and so on. Upon having sensed the toxic substances, oil, mold, or the like, an alarm is automatically issued thereby.

7 Claims, 33 Drawing Sheets

(51) Int. Cl.
*A01K 61/10* (2017.01)
*A01K 63/06* (2006.01)
*G06T 7/00* (2017.01)

(56) References Cited

FOREIGN PATENT DOCUMENTS

| | | | |
|---|---|---|---|
| JP | H07-063747 | A | 3/1995 |
| JP | H09-229924 | A | 9/1997 |
| JP | H11-295203 | A | 10/1999 |
| JP | 2001-324463 | A | 11/2001 |
| JP | 2002-257815 | A | 9/2002 |
| JP | 2003-334537 | A | 11/2003 |
| JP | 2004-125753 | A | 4/2004 |
| JP | 2012-098150 | A | 5/2012 |
| JP | 2013-217680 | A | 10/2013 |
| JP | 2014-228457 | A | 12/2014 |
| JP | 2015-127644 | A | 7/2015 |

* cited by examiner

[Table 1]

[Table 2]

| alarm | set blocks | timer setting [s] |
|---|---|---|
| caution1 | 5 | 120 |
| caution2 | 4 | 180 |
| caution3 | 3 | 240 |
| abnormal | 2 | 300 |

[Table 3]

Fig. 17

[Table 4]

test fish

| name | body length | characteristics | general evaluation |
|---|---|---|---|
| cyprinodont | ≦ 2.8cm | The fish is widely cultured and easily available in Japan. Original is Japanese rice fish, and genetic factors are exclued. Not large body size. It well reacts against a fine amount of toxic substances. | ◎ |
| zebra fish | ≦ 5cm | The fish is generally sold by tropical fish seller. Not large body length and easily used. | ○ |
| guppy | ≦ 6cm | The fish is generally sold by tropical fish seller. Not large body length and easily used. | ○ |
| fathead minnow | ≦ 8cm | The fish is produced in North America, but rarely available in Japan. | △ |
| rainbow trout | ≦ 10cm | Too large body length. Poor reaction against toxic substances. | △ |
| O. masou | ≦ 8cm | Sensitive to water temperature, may die at 20 °C or more. Not easy to be used. | △ |
| carassius | ≦ 10cm | Too large body length. Poor reaction against toxic substances. | △ |
| A. melanogaster | ≦ 8cm | Rarely cultured, poor availability. | △ |
| gold fish | ≦ 6cm | The fish has been crossbread from carassius to be admired. Unkwon torelance. Uneven reation against toxic substances. | △ |

Fig. 18

[Table 5]

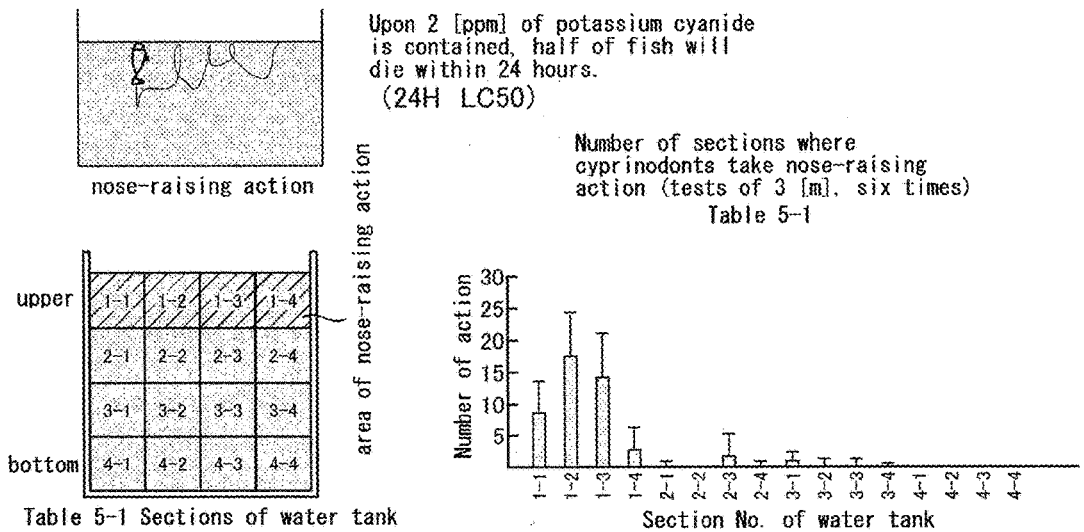

Table 5-1 Sections of water tank

What section cyprinodonts swim when 2 [ppm] of potassium cyanide is exposed thereto has been examined repeatedly six times.

Upon 2 [ppm] of potassium cyanide is contained, half of fish will die within 24 hours.
(24H LC50)

Number of sections where cyprinodonts take nose-raising action (tests of 3 [m], six times)
Table 5-1

Table 2 shows an average value thereof. At that time, no nose-raising action has been recognized.

Presented by: bioassay laboratory
(Yamamoto Lab. Of the Kyusyu University)

Fig. 19

[Table 6]

| alarm | sensed blocks | timer setting [s] | operation time |
|---|---|---|---|
| caution1 | 10 | 30 | 0.5 |
| caution2 | 8 | 45 | 0.5 |
| caution3 | 6 | 60 | 0.5 |
| abnormal | 4 | 75 | 0.5 |

Fig. 20

[Table 7]

light oil concentration 1mg/L　　　　　　　　Sensitivity: Low

| time [s] | temperature | | | | | |
|---|---|---|---|---|---|---|
| | 5° C | 15° C | 20° C | 25° C | 30° C | 35° C |
| 0 | 277 | 259 | 274 | 274 | 251 | 294 |
| 10 | 283 | 296 | 305 | 331 | 355 | 355 |
| 20 | 282 | 306 | 306 | 399 | 391 | 386 |
| 30 | 284 | 309 | 306 | 420 | 409 | 412 |
| 40 | 286 | 310 | 306 | 438 | 430 | 427 |
| 50 | 288 | 312 | 309 | 451 | 439 | 440 |
| 60 | 290 | 316 | 313 | 457 | 450 | 447 |
| 70 | 291 | 322 | 320 | 459 | 458 | 453 |
| 80 | 292 | 328 | 326 | 458 | 468 | 458 |
| 90 | 294 | 333 | 332 | 459 | 473 | 462 |
| 100 | 296 | 339 | 342 | 461 | 477 | 464 |
| 110 | 298 | 345 | 352 | 462 | 481 | 466 |
| 120 | 301 | 350 | 362 | 463 | 482 | 468 |
| 130 | 303 | 356 | 367 | 464 | 484 | 471 |
| 140 | 306 | 361 | 375 | 465 | 486 | 472 |
| 150 | 308 | 366 | 380 | 466 | 488 | 473 |
| 160 | 310 | 371 | 385 | 467 | 489 | 475 |
| 170 | 312 | 375 | 390 | 468 | 490 | 476 |
| 180 | 315 | 379 | 394 | 469 | 491 | 477 |
| 190 | 317 | 383 | 398 | 469 | 492 | 477 |
| 200 | 319 | 387 | 402 | 470 | 493 | 478 |
| 210 | 321 | 389 | 405 | 471 | 494 | 479 |
| 220 | 322 | 392 | 408 | 471 | 495 | 480 |
| 230 | 324 | 394 | 411 | 472 | 495 | 481 |
| 240 | 326 | 396 | 413 | 472 | 496 | 480 |
| 250 | 327 | 398 | 416 | 473 | 496 | 481 |
| 260 | 328 | 399 | 418 | 474 | 496 | 482 |
| 270 | 329 | 401 | 420 | 474 | 497 | 483 |
| 280 | 330 | 402 | 421 | 474 | 497 | 482 |
| 290 | 332 | 404 | 423 | 475 | 497 | 483 |
| 300 | 333 | 405 | 424 | 475 | 497 | 482 |

Fig. 22

[Table 9]

light oil concentration 1mg/L    Sensitivity: High

| time [s] | temperature | | | | | |
|---|---|---|---|---|---|---|
| | 5° C | 15° C | 20° C | 25° C | 30° C | 35° C |
| 0 | 343 | 309 | 343 | 318 | 344 | 393 |
| 10 | 361 | 357 | 409 | 398 | 463 | 434 |
| 20 | 368 | 366 | 414 | 412 | 502 | 459 |
| 30 | 376 | 370 | 418 | 471 | 554 | 487 |
| 40 | 381 | 375 | 423 | 521 | 591 | 512 |
| 50 | 383 | 380 | 426 | 564 | 605 | 532 |
| 60 | 385 | 385 | 430 | 576 | 623 | 547 |
| 70 | 388 | 396 | 436 | 585 | 637 | 559 |
| 80 | 390 | 418 | 444 | 594 | 651 | 565 |
| 90 | 393 | 432 | 453 | 603 | 659 | 575 |
| 100 | 396 | 453 | 464 | 610 | 666 | 583 |
| 110 | 399 | 471 | 474 | 615 | 671 | 590 |
| 120 | 403 | 486 | 485 | 619 | 675 | 596 |
| 130 | 406 | 497 | 496 | 623 | 678 | 602 |
| 140 | 410 | 507 | 507 | 625 | 680 | 605 |
| 150 | 413 | 516 | 516 | 627 | 683 | 609 |
| 160 | 417 | 523 | 527 | 629 | 685 | 611 |
| 170 | 420 | 529 | 539 | 631 | 689 | 614 |
| 180 | 425 | 534 | 551 | 633 | 693 | 618 |
| 190 | 429 | 538 | 562 | 636 | 698 | 620 |
| 200 | 434 | 541 | 573 | 637 | 699 | 622 |
| 210 | 438 | 545 | 582 | 638 | 703 | 623 |
| 220 | 442 | 547 | 591 | 640 | 703 | 626 |
| 230 | 446 | 549 | 599 | 642 | 703 | 628 |
| 240 | 449 | 551 | 604 | 643 | 703 | 630 |
| 250 | 452 | 553 | 610 | 644 | 704 | 633 |
| 260 | 456 | 555 | 614 | 645 | 705 | 633 |
| 270 | 459 | 556 | 618 | 647 | 706 | 635 |
| 280 | 462 | 557 | 621 | 647 | 706 | 636 |
| 290 | 465 | 558 | 625 | 648 | 707 | 638 |
| 300 | 468 | 559 | 627 | 649 | 709 | 640 |

Light oil: 0.00001mg/L, 15 degree C, three steps of sensitivity

[Table 12]

Kerosene: 0.01mg/L, 15 degree C, three steps of sensitivity

[Table 13]

Kerosene: 0.00001mg/L, 15 degree C, three steps of sensitivity

Fig. 27 [Table 14]

Gasoline: 0.01mg/L, 15 degree C, three steps of sensitivity

Gasoline: 0.00001mg/L, 15 degree C, three steps of sensitivity

Fig. 29 [Table 16]

Engine oil: 0.01mg/L, 15 degree C, three steps of sensitivity

[Table 17]

Engine oil: 0.00001mg/L, 15 degree C, three steps of sensitivity

Geosmin: 0.01mg/L, 15 degree C, three steps of sensitivity

[Table 19]

Geosmin: 0.000001mg/L, 15 degree C, three steps of sensitivity 2-methylisoborneol (2-MIB): 0.00001mg/L, 15 degree C, three steps of sensitivity Fig. 35 [Table 22]
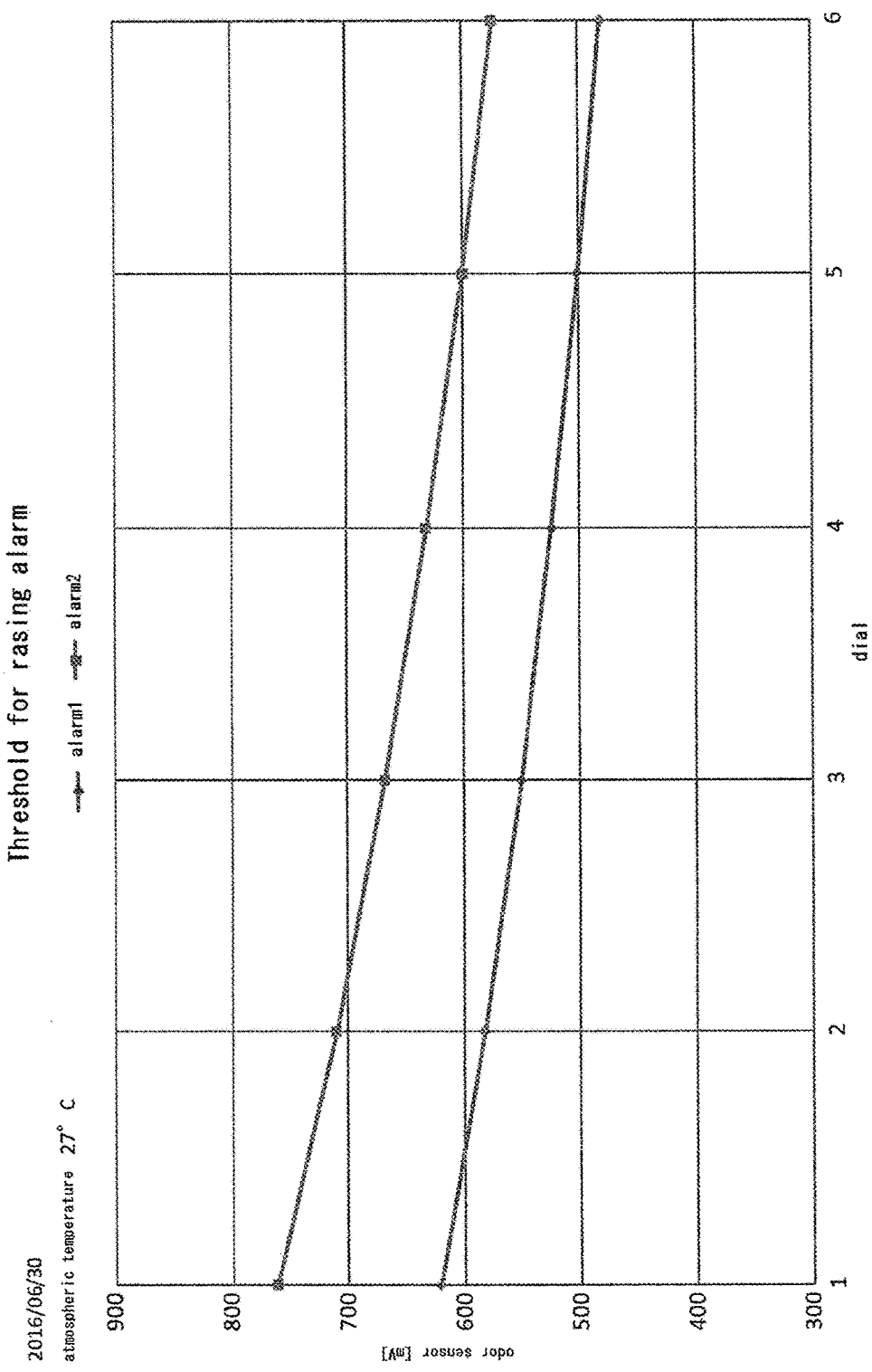

AUTOMATIC WATER QUALITY SURVEILLANCE APPARATUS

BACKGROUND OF THE INVENTION

1. Field of the Invention

The present invention relates to an automatic water quality surveillance apparatus sensing corresponding substances contained in raw water causing a water pollution accident.

2. Description of the Related Art

Accidents that toxic substances are contaminated to raw water, such as river flowing water, lake water, and ground water, have been occurred. There is also a case where formaldehyde, which is a carcinogen (a substance that may cause cancer), has been sensed from the Tone-Gawa River system in 2012 and 870,000 people have been without water according to the stop suspension of the water intake therefrom.

The toxic substances are too frequent to enumerate and include, for example, chlorinated organic compounds (e.g. PCB: polychlorinated biphenyl), harmful heavy metals (e.g. mercury, cadmium, lead, zinc, and hexavalent chromium), dioxin called as the worst in the history, potassium cyanide of acute toxicity, agricultural chemicals, and so on.

There also may be possibility that the water in the river or the like contains compounds of dangerous substances produced by chemical reaction between two or more of the above simple substances.

In public water supply, food factories, or the like, it is required to do one's best to deal with this matter. Contamination of the raw water by the toxic substances should be promptly sensed so as to stop the water intake related thereto.

For this reason up to now, bioassay methods for surveying the toxic substances utilizing aquatic organisms (e.g. fish, crustaceans, and algae, or the like.) have been widely recognized and used.

In recent years, apparatuses for rearing fish within surveillance water tanks so as to visually and/or automatically survey the fish have been widely practically used.

Contamination by toxic substances may be a matter of life and death of human beings in some cases. Accordingly, the Water Supply Law requires installation of the bioassay method. And, Article 23, paragraph 1 thereof declares an emergency stop of water supply and recites that when water supply utilities know city water thereof may be prejudicial to human health the water supply utilities shall take measures of immediately stopping water supply thereby and ensuring that every stakeholder knows that it is danger to use the city water.

The penal law is severely established. Any person who fails to comply with the penal provision of Article 23, paragraph 1 (Article 52 of the water law) shall be punished by imprisonment with work for not more than three years or by a fine of not more than 3,000,000 yen.

However practically, fewer pollution accidents of raw water are caused by contamination by acute toxicity and much more pollution accidents of raw water concern oil spill accidents and/or complaints of mold odors, and so on.

(A classification table of water pollution accidents is shown in FIG. 14 (Table 1).)

Now, automatic oil measurement methods sensing oil in raw water include: a hexane extraction method measuring mass of substances extracted by hexane; an ultraviolet fluorescence method using ultraviolet irradiation; an orgastor method using a polymer membrane; a crystal oscillation method measuring mass of odor molecules adsorbed by an odor-sensitive membrane; gas chromatography, and so on.

Furthermore, as methods of sensing an oil film, there are: a relative permittivity method of sensing floating oil as the oil film; and a beam reflection method of irradiating light to a water surface so as to measure reflected light therefrom; and so on.

All apparatuses related to the above have too large sizes and/or are too expensive. There is no low priced, small, and high performance device capable of being included in an automatic water quality surveillance apparatus according to the presently used bioassay method (organism verification method) analyzing toxic substances based on activities of fish or the like.

Bioassay apparatus makers and oil sensing apparatus makers have different technical fields from each other. So, no one devises nor tries to integrate toxic substance sensing and oil sensing with each other.

In this context, requests for development have been frequently heard from the user side. This is because the user side considers that, if the toxic substance sensing apparatus and the oil sensing apparatus have been united into one apparatus, both of installing space and cost thereof can be less in total.

Once oil entered a raw water receiving well, a filtration pond, or the like, a remaining odor thereof cannot removed even when the cleaning thereof has been performed. This is troublesome since complaints of inhabitants using the city water must be made.

For this reason, the oil sensing apparatuses have been installed. They are, however, expensive and require both wide installing spaces and difficult maintenance management. Many requests have been received for a while, the requests having asked for performing the oil sensing also by means of the toxic substance sensing apparatus according to the bioassay with fish which has been practically used.

The present inventor has been performed exposure tests on cyprinodonts using kerosene and engine oil as the oil.

With respect to water having prepared by mixing 60 [mL] of kerosene into 12 [L] of sample water (24 or more [hours] reserved pure water/city water), the cyprinodonts have not died but stopped moving, resulting in having issued an alarm.

Similarly, with respect to water having prepared by mixing 60 [mL] of engine oil into 12 [L] of the sample water, the cyprinodonts have not died but have stopped moving, resulting in having issued an alarm.

Whereas, with respect to a fine amount oil (e.g. 1.0 [ml] of the above mentioned kerosene/engine oil), the cyprinodonts have normally kept moving, resulting in having issued no alarm.

In the above tests and also in the following test, cultured cyprinodonts (scientific name: "*Oryzias latipes*" so called as a "himedaka" in Japan) have been used as the cyprinodonts. Various kinds of small organisms, however, can be used for the bioassay such as cyprinodonts, fathead minnows, zebra fish, daphnias of invertebrates, crustaceans, and so on.

In Japan, "himedaka"s are widely cultured and easily available stably. So, they have been used in the tests. Alternatively, one or more of the above mentioned small organisms may be adapted instead thereof.

Complaints of inhabitants using city water with respect to a mold odor are many as the same as those with respect to an oily odor.

Regarding the mold odor, cause thereof is not the mold itself. The cause is substances produced by algae propagating in a city water source such as a dam, a lake, a reservoir, a river, or the like.

As troublesome kinds, Phormidium, Anabaena, and so on are known. When these have increased to produce geosmin and 2-MIB (2-methylisoborneol), thereby generating the mold odor.

LIST OF REFERENCES

Reference 1: Japanese patent application Laid-open on No. Heisei 11-295203;

Reference 2: Japanese patent application Laid-open on No. Heisei 07-063747;

Reference 3: Japanese patent application Laid-open on No. Heisei 09-229924;

Reference 4: Japanese patent application Laid-open on No. 2002-257815;

Reference 5: Japanese patent application Laid-open on No. 2004-125753;

Reference 6: Japanese patent application Laid-open on No. 2003-334537;

Reference 7: Japanese patent application Laid-open on No. 2015-127644;

Reference 8: Japanese patent application Laid-open on No. 2014-228457; and

Reference 9: Japanese patent application Laid-open on No. 2012-98150.

OBJECTS AND SUMMARY OF THE INVENTION

An object of the present invention is to solve the problem of water pollution accidents by providing an odor sensor sensing an oily odor and/or a mold odor with an organism surveillance apparatus according to the bioassay method of automatically sensing contamination to raw water (e.g. river flowing water, lake water, ground water, and so on.) by toxic substances.

As the following table, kinds of water pollution accidents have been investigated.

(Breakdown of phenomena related to total number of water pollution accidents (1006 accidents in total) (Page 34 of "Guide plan 2002 for surveying sudden water pollution", The Japan Water Works Association)

In order to solve the object, an automatic water quality surveillance apparatus 1 defined in claim 1 comprises:

a water tank for fish 4d always and continuously receiving raw water so as to rear a plurality of cyprinodonts 4e therein, the raw water including: river flowing water; lake water; and ground water; and a CCD video camera photographing abnormal behavior when the raw water contains toxic substances therein, the abnormal behavior including: a first case where the plurality of cyprinodonts 4e form a fixed group that does not move; a second case where the plurality of cyprinodonts 4e take at least one of repelling action and madly-rushing action; and a third case where the plurality of cyprinodonts die, wherein:

the automatic water quality surveillance apparatus performs digital conversion on image signals from the CCD video camera, and arranges 56 blocks in total (vertically 7 blocks and horizontally 8 blocks) onto the entire surface of the water tank for fish;

sensing dots for every block of the 56 blocks are configured with 64 sensing dots (vertically 8 sensing dots and horizontally 8 sensing dots), upon at least one of the plurality of cyprinodonts touching with at least one of the 64 sensing dots, a block to which the touched at least one of the 64 sensing dots belongs is displayed on a monitor TV 1e and is counted; and algorithm for automatically alarming is configured according to a system of: defining a number of blocks to be sensed within a predetermined time; and issuing an alarm when the defined numbers of blocks are not sensed within the predetermined time.

FIG. 15 (Table 2) shows a setting example thereof.

The set times and the set number of blocks may not be fixed but can be freely set up taking water quality and/or the state of the site into consideration.

Alarms are configured with four steps of: Caution_level 1; Caution_level 2; Caution_level 3; and Abnormal. Predetermining a respective time and a respective number of blocks for every step of the four steps enables to issue an automatic alarm in a stepwise manner.

Upon cyprinodonts 4e return moving normally even if an alarm of at least one of Caution_level 1, Caution_level 2, and Caution_level 3 has been issued, the alarm will be automatically canceled. FIG. 16 (Table 3) shows surveillance flows related thereto.

If an abnormality alarm has been issued, a fixed amount of the raw water within the water tank for fish is stored as sampling water by automatically opening a solenoid valve.

The surveillance water tank 4 in this automatic water quality surveillance apparatus 1 includes: the water-receiving tank 4m; the odor-sensing water tank 4a; and the water tank for fish 4d. The odor sensor sensing element 3 is provided in the odor-sensing water tank 4a. The odor sensor control unit 2 is provided on a front surface of the apparatus. A mold odor is sensed by the odor sensor connected by means of the cable 3g connecting therebetween.

The heater 4b heating the raw water circulating through the odor-sensing water tank 4a is included.

The odor-sensing water tank 4a is isolated from open air except an inlet and an outlet of the raw water.

The odor sensor includes: the odor sensor sensing element 3; and the odor sensor control unit 2; the odor sensor sensing element 3 and the odor sensor control unit 2 are separately arranged and are connected to each other by means of the cable 3g. The odor sensor sensing element 3 is arranged within the odor-sensing water tank 4a.

A semiconductor sensor measuring a change of electric resistance caused by chemical absorption of reducible gas existing on a surface of a metal oxide semiconductor is utilized as the odor sensor sensing element 3.

The odor sensor control unit 2 includes: the sensitivity-adjusting variable resistor 2a adjusting odor sensitivity; and the sensitivity range-adjusting knob 2b.

The LED display 2d displaying a level of odor concentration that the odor sensor sensing element is sensing; and the concentration LED bar 2c numerically displaying the odor concentration are included.

Signals via the cable 3g from the odor sensor sensing element 3 are controlled by means of the microcomputer 2h implemented within the odor sensor control unit 2; the microcomputer is configured for: generating a conversion program for displaying sensing data sensed by the odor sensor sensing element 3 on the LED display 2d; and making the concentration LED bar 2c perform display according to the concentration obtained by stepped processing operation on the sensing data using the sensitivity-adjusting variable resistor 2a of a rotary type.

The odor-sensing water tank 4a is provided in a channel at a side of the water tank for fish receiving the raw water toward the water tank for fish 4d that rears the fish.

The odor sensor control unit 2 is juxtaposed to the display panel 1d of the automatic water quality surveillance apparatus.

The automatic water quality surveillance apparatus as defined in claim 2, in addition to claim 1 further comprising: the heater 4b heating the raw water circulating through the odor-sensing water tank 4a; and the thermostat 4k automatically ON/OFF switching a power source of the heater 4b, thereby controlling temperature of the raw water within the odor-sensing water tank 4a.

The automatic water quality surveillance apparatus as defined in claim 3 or 4 in addition to any one of claims 1 to 2, wherein the heater is composed of a ceramic heater.

The automatic water quality surveillance apparatus as defined in any one of claims 5 to 7 in addition to any one of claims 1 to 3, wherein: the odor sensor control unit performs analysis; and the automatic water quality surveillance apparatus further comprises the alarming device 2k automatically outputting an alarm to the outside when alarming conditions are fulfilled.

Effect of Invention

As mentioned above, the automatic water quality surveillance apparatus 1 according to the present invention provides the odor sensor sensing an oily odor and/or a mold odor within the odor-sensing water tank 4a though which raw water circulates. Accordingly, first effect can be obtained, the first effect enabling to sense inflow of oil and/or mold odor substances to the raw water.

The automatic water quality surveillance apparatus sensing with the fish inflow of toxic substances into the raw water is provided with: the odor-sensing water tank 4a through which the raw water circulates. And, the odor-sensing water tank 4a includes:

the odor sensor sensing element 3 sensing an odor (e.g. an oily odor, a mold odor, and so on.); the odor sensor control unit 2; and the odor sensor provided with the cable 3g connecting the odor sensor sensing element 3 and the odor sensor sensing element 3.

Accordingly, second effect can be obtained, the second effect enabling to sense oil and/or mold odor substances in accordance with an odor thereof in addition to toxic substances.

Namely, the present inventor has shouldered studies covering from research and development to practical application of automatic water quality surveillance apparatuses with cyprinodonts for a long time.

In order to solve run-off accidents of oil and complaints caused by a mold odor, which are also subject matters of these days of water examiners, the odor sensor is provided with the automatic water quality surveillance apparatus sensing with cyprinodonts that has been already commercially produced and has been practically used widely. Accordingly, there is another merit that the odor sensor can be additionally provided for also an automatic water quality surveillance apparatus with cyprinodonts that has been already operated.

The odor sensor according to the present invention is small and lightweight, and can be provided within the automatic water quality surveillance apparatus. So, it is able to narrow a space in comparison with the prior oil sensing apparatus.

In a water supply facility (e.g. a machine room and/or a water examination room of a water purification plant), many measuring and/or inspection instruments are located normally. It can be said that space-saving becomes a large benefit also from the management side thereof.

Furthermore, the odor sensor is less expensive than the prior oil sensing apparatus. In other words, costs for the apparatus can be reduced.

Including the heater 4b heating the raw water circulating through the odor-sensing water tank 4a enables to promote the sensing performance. This is because the heating promotes decomposition of an oily odor and/or a mold odor to make the odor stronger.

Including the thermostat 4k automatically ON/OFF switching the power source of the heater 4b so as to control temperature of the raw water within the odor-sensing water tank 4a enables to stabilize the temperature of the raw water within the odor-sensing water tank 4a within a fixed range, thereby improving the stability of the sensing precision of an oily odor and/or or a mold odor. This is because a change of the raw water temperature is lessened.

Including: the temperature sensor 1h measuring the temperature of the raw water within the odor-sensing water tank 4a; and the thermometer 1f displaying the temperature of the raw water enables to confirm the abnormality of the heater 4b and/or the thermostat 4k with eyes.

It is also possible to output data of the water temperature, thereby recording the outputted data onto the personal computer 2i or the like.

Adapting the feature that the odor-sensing water tank 4a is isolated from open air except the inlet and outlet of the raw water enables to prevent from the deterioration of sensing precision of and/or erroneous sensing of the odor sensor caused by another odor approaching from the open air.

The following effect can be obtained by adapting the feature that the odor sensor includes: the odor sensor sensing element 3; and the odor sensor control unit 2; the odor sensor sensing element 3 and the odor sensor control unit 2 are separately arranged and are connected to each other by means of the cable 3g, and further that the odor sensor sensing element 3 is arranged within the odor-sensing water tank 4a.

That is, the odor sensor sensing element 3 is installed in an inferior space where moisture, vapor, and/or humidity generate, and may be more rapidly deteriorated than normal usage thereof. However, the maintenance work thereof is less expensive and easy because only the odor sensor sensing element 3 can be exchanged.

Signals via the cable 3g from the odor sensor sensing element 3 are controlled by means of the microcomputer 2h implemented within the odor sensor control unit 2; the microcomputer 2h is configured for generating the conversion program for displaying sensing data sensed by the odor sensor sensing element 3 on the LED display 2d and/or the concentration LED bar 2c. The microcomputer 2h is further configured for generating another program for the alarm-outputting circuit according to an interrupt function of performing the stepped processing operation on the sensing data using a rotary switch of the sensitivity-adjusting variable resistor 2a.

The data can be outputted there-from. This feature can contribute also to power saving because remote supervision of the apparatus can be done by means of connection via the Internet or the like.

The odor sensor control unit 2 includes: the rotary switch of the sensitivity-adjusting variable resistor 2a and/or the sensitivity range-adjusting knob 2b each adjusting the odor sensitivity. So, erroneous sensing can be prevented and it is possible to select an optimum value of the sensitivity for an oily odor and/or a mold odor.

Including: the LED display 2d displaying the level of odor concentration that the odor sensor sensing element is sensing; and the concentration LED bar 2c displaying the odor concentration enables to confirm the operational function of the odor sensor sensing element 2 with eyes.

If the odor sensor senses an/a oily/mold odor, the microcomputer 2h in the odor sensor control unit 2 performs analysis thereof; and the automatic water quality surveillance apparatus further comprises the alarming device automatically outputting an alarm to the outside when alarming conditions are fulfilled.

With this feature, even if a manager of the apparatus is not near the apparatus, contamination of oil and/or mold can be sensed caused by alarming sound and/or alarming light, thereby allowing prompt response thereto.

The odor-sensing water tank 4a is provided in the middle of the raw water channel of the water tank for fish 4d that rears the fish. Due to this, the apparatus can be made compact.

The odor-sensing water tank 4a is provided in the channel at the side of the water tank for fish receiving the raw water toward the water tank for fish 4d that rears the fish. And, the heater 4b is included, the heater 4b preventing the cyprinodonts 4e from becoming suspended animation and/or stopping behavior thereof caused by water temperature drop. Accordingly, functions of the apparatus can be exhibited.

As shown in FIG. 3, the odor sensor control unit 2 may be stored in a box or on the display panel 1d.

The odor sensor control unit 2 is juxtaposed to the display panel 1d of the automatic water quality surveillance apparatus. Due to this, both surveillance and operation are easy, and erroneous operation can be prevented.

BRIEF DESCRIPTION OF THE DRAWINGS

FIG. 17 is a table showing evaluation of test fish used in Japan (Table 4);

FIG. 18 is a test data showing that cyprinodonts take unique action based on the kind of toxic substances (Table 5);

FIG. 19 is a table showing a setting example for defining a number of blocks to be sensed within a predetermined time, and issuing an alarm when the defined numbers of blocks are not sensed within the predetermined time (Table 6);

FIG. 20 is a test table showing sensing performance of an odor sensor (Table 7);

FIG. 22 is a measurement table whose sensitivity has been made to be the highest by means of both a sensitivity-adjusting variable resistor and the sensitivity range-adjusting knob of the odor sensor control unit (Table 9);

FIG. 35 is data showing thresholds of raising alarms (Table 22).

DETAILED DESCRIPTION OF THE PREFERRED EMBODIMENTS

Embodiments of the present invention will now be described with reference to the accompanying drawings. In particular, an automatic water quality surveillance apparatus 1 with fish provided with an odor sensor will now be explained in detail.

Embodiment 1

Figure 1:
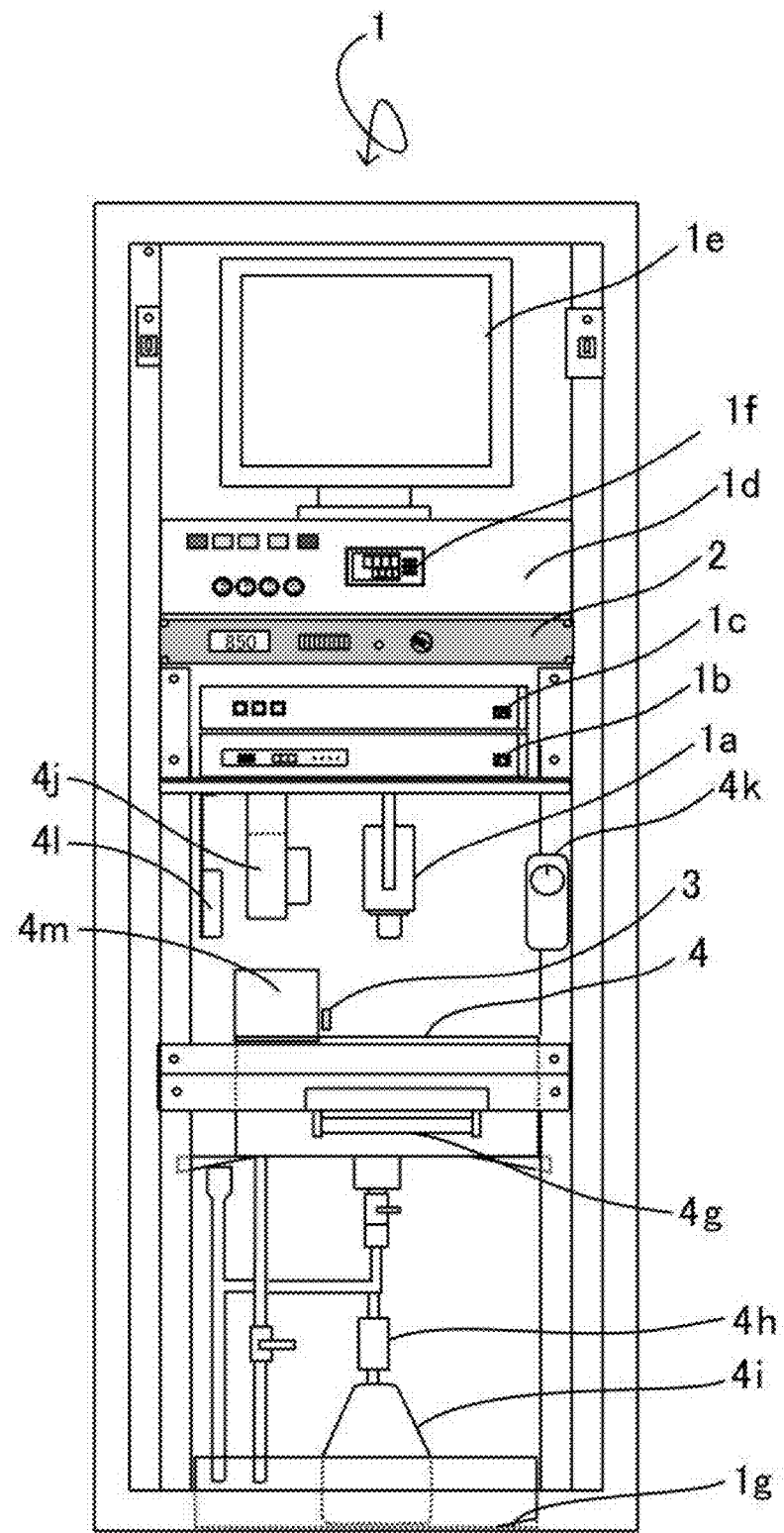
FIG. 1 is an outline view showing an automatic water quality surveillance apparatus in Embodiment 1.
Figure 2:
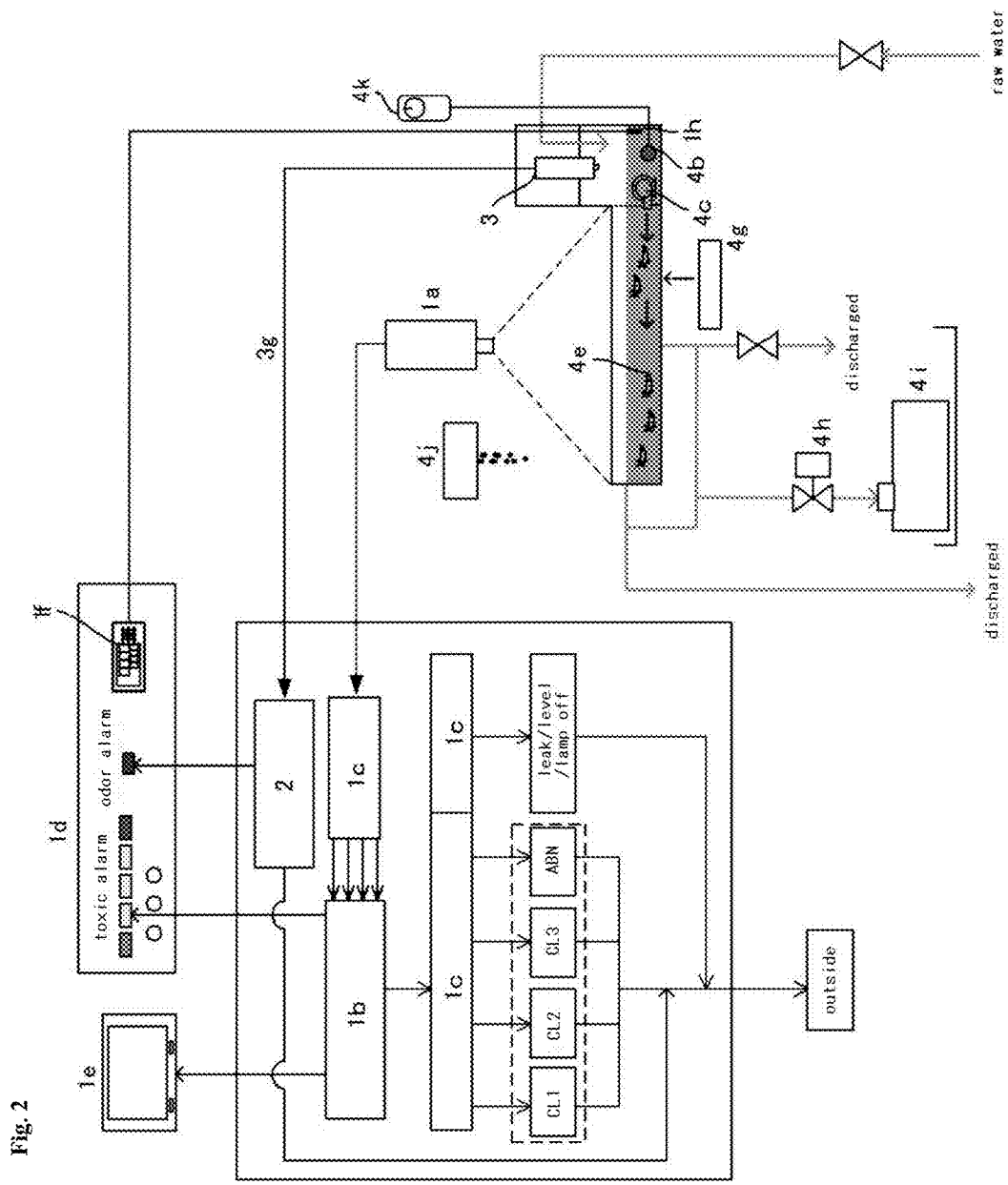
FIG. 2 shows a process of a surveillance water tank of the automatic water quality surveillance apparatus in Embodiment 1.
Figure 3:
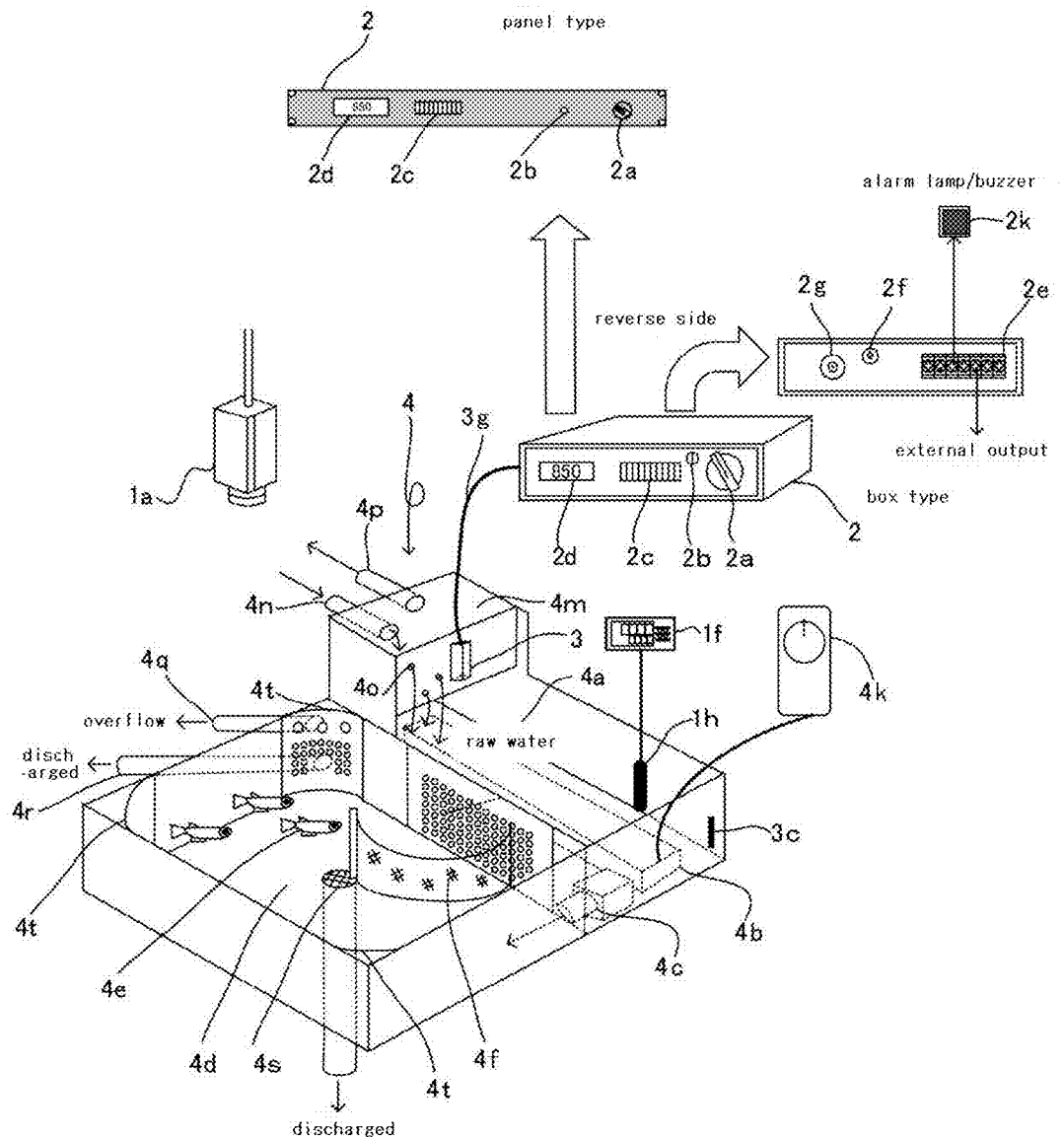
FIG. 3 is: an outline view of the surveillance water tank in the automatic water quality surveillance apparatus in Embodiment 1; and a block diagram showing an odor sensor control unit connected by a cable to an odor sensor sensing element provided in an odor-sensing water tank.

First, referring to FIGS. 1 through 3, an apparatus is explained, the apparatus being a prior automatic surveillance apparatus 1 with fish to which the odor sensor in Embodiment 1 should be applied.

The surveillance water tank of the automatic surveillance apparatus 1 with fish includes: the water-receiving tank 4m; the odor-sensing water tank 4a used also as a pump tank; and the water tank for fish 4d.

The raw water is supplied from the water inlet 4n into the water-receiving tank 4m to be stored therein.

The plurality of supply holes 4o are opened in a step form through the water-receiving tank 4n. So, from the supply holes 4o opened in the step form, the raw water is supplied to the odor-sensing water tank 4a.

If a first supplied amount from the water inlet 4n is more than a second supplied amount from the supply holes 4o to the odor-sensing water tank 4a, the raw water is drained from the water-receiving tank's overflow pipe 4p of the water-receiving tank 4m.

If the level of raw water supplied into the odor-sensing water tank 4a is not less than 5 [cm] of an operable level of the underwater pump 4c, the raw water is sucked by the underwater pump 4c to be forcibly discharged against an inner wall of the water tank for fish 4d.

Among a group of cyprinodonts reared within the water tank for fish 4d, cyprinodonts 4e tends to willingly appear at a position where the raw water is discharged by the underwater pump 4c.

This is because many of fish including the cyprinodonts have habit of swimming toward the discharged water flow.

Cyprinodonts have the first scientific name of "*Oryzias latipes*", and are originated from Japanese rice-fish. The word of "*Oryzias*" is derived from the second scientific name "*Oryza sativa*" of rice.

Japanese rice-fish is nowadays protected as an endangered animal.

Cyprinodonts as test fish, which are cultured Japanese rice-fish for admiration, are largely cultured and genuine fish whose hereditary factors are excluded. OECD (Organization for Economic Cooperation and Development) has specified them as test fish. Furthermore, they are small fish and sensitively react with toxic substances.

"*Oryzias latipes*" is fish which widely lives in a rice-producing district from East South Asia to East Asia, and does not live in Western Europe. So in Western Europe, small fish such as fathead minnows and zebra fish is used instead thereof.

There are examples using goldfish or the like. However, since the goldfish has been repeatedly crossbred to be admired by human beings, tolerance thereof to toxic substances is not known. Accordingly, the goldfish or the like may be considered not to be suitable for the test fish related to this kind.

As mentioned at the beginning of the specification, there are various kinds of small organisms that can be used for the bioassay such as cyprinodonts, fathead minnows, zebra fish, daphnias of invertebrates, crustaceans, and so on.

FIG. 17 (Table 4) shows evaluation of test fish used in Japan.

Cyprinodonts have habit of swimming toward a water flow. When the raw water flows along the inner wall surface of the water tank for fish 4d, the group does not remain at a fixed position but changes a place where the group acts.

If the level of the water tank for fish 4d is not less than 8 [cm], the raw water is drained from the surveillance water tank water tank for fish's overflow pipe 4q.

The water level-adjusting pipe 4r is connected to a lower portion of the surveillance water tank water tank for fish's overflow pipe 4q, and a first extension pipe of the water level-adjusting pipe 4r and a second extension pipe of the drain port 4s are connected and piped to a position of lower limit level (5 [cm]) of the surveillance water tank 4.

If the level is not greater than 5 [cm] of the lower limit level, drainage of the raw water is stopped so as to maintain the lower limit level (5 [cm]).

Since the lower limit level (5 [cm]) of the water tank for fish 4d is maintained, the group of cyprinodonts do not die from too less water.

The raw water flows along the inner wall surface of the water tank for fish 4d to pass through meshes of the capture net 4f.

The semicircle boards 4t are attached to three corners of the water tank for fish 4d, and the raw water smoothly flows to perform centrifugal separation. Due to this, feed residues, droppings, wastes, or the like are automatically collected to a central portion of the water tank for fish 4d to be always discharged from the drain port 4s. In other words, the water tank for fish 4d is automatically purified so that the raw water can be always received in a fresh state.

If the semicircle boards 4t are not installed, whirlpools may occur at the corners, the feed residues, the droppings, the wastes, or the like are stuck and fixed at the corners to cause chemical reaction, such as generation of nitrate nitrogen or the like, which may cause the cyprinodonts 4e to die.

The toxic substance sensing using the automatic water quality surveillance apparatus according to the present invention assumes that the cyprinodonts 4e of the test fish are fine and live for a long period of time, and further that the cyprinodonts 4e react when toxic substances are contaminated into the raw water, thereby making the apparatus display effects thereof.

It may be said that an apparatus provided with a water tank for fish whose living environment is not well-designed is not suitable. This is because this apparatus may cause the fish to die even if the toxic substances are not contaminated, resulting in giving erroneous judgment information to the user thereof.

Figure 10:
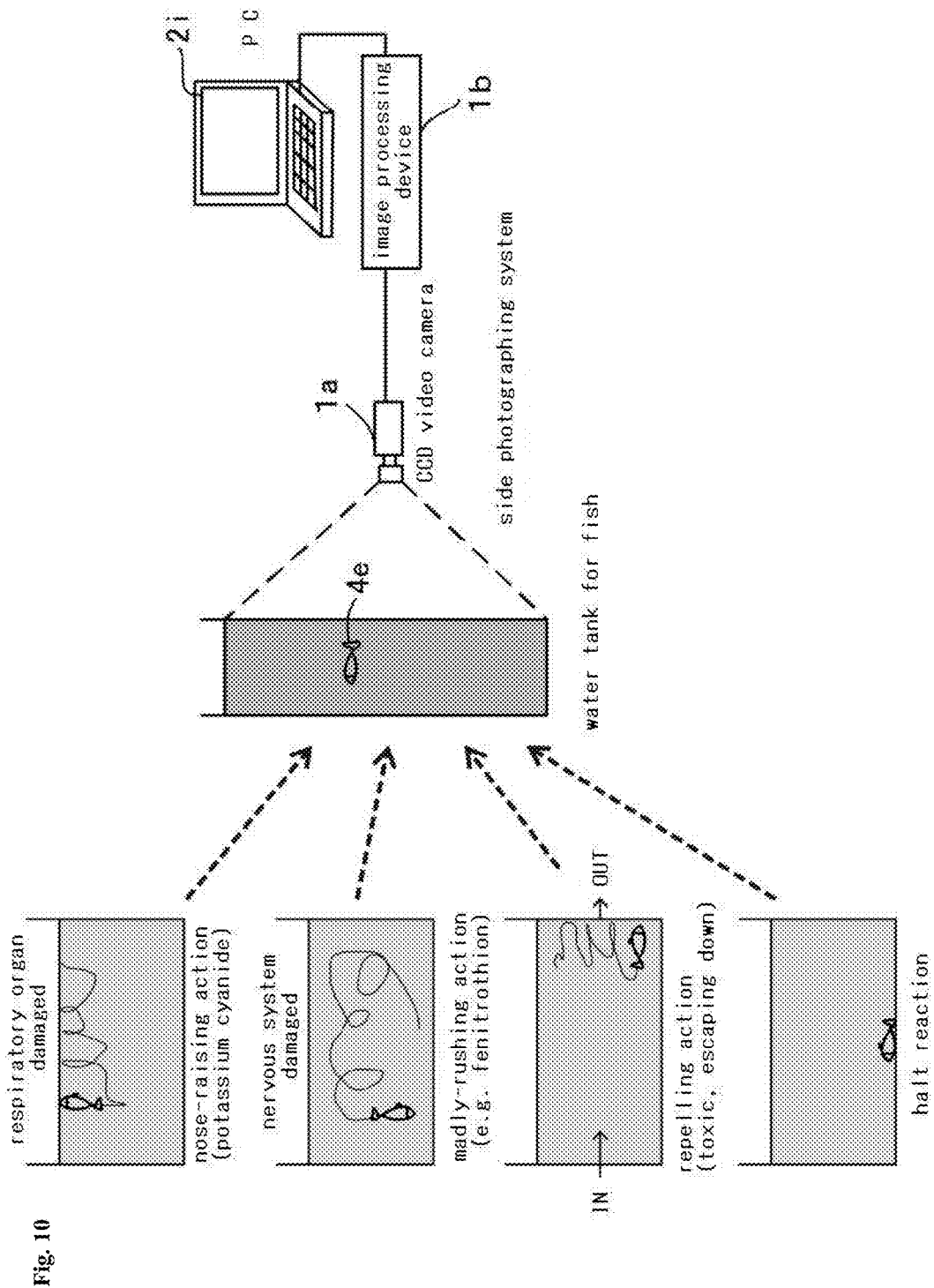
FIG. 10 shows a side photographing system.

Referring to FIG. 10, it is clear that the cyprinodonts 4e take unique action based on the kind of toxic substances.

For example, potassium cyanide damages respiratory organs, the cyprinodonts cannot carry out bronchial respiration, but open mouths thereof to carry out aerial respiration.

This reaction is called as "nose-raising" action.

Fenitrothion, which is pesticide belonging to organ phosphorus pesticide, damages nervous systems of the cyprinodonts. As a result, madly-rushing action or the like may be observed.

Furthermore, the cyprinodonts may take repelling action of escaping in a downstream direction, halt reaction, and so on.

At the beginning of the invention, the present inventor has devised: putting one cyprinodont 4e into a rearing tank; photographing it by means of a CCD video camera 1a from a side wall; and judging the nose-raising action, the madly-rushing action, the repelling action, and the halt reaction. However, when feeds have floated on a water surface, the cyprinodont has moved to the water surface and has taken reaction similar to the nose-raising action, having resulted in issuing an erroneous alarm.

The following problems have occurred. That is, the one cyprinodont 4e has died young in about one month. Algae have adhered to an inner surface of the tank, which obstructs photographing by means of a CCD video camera 1a.

In order to solve the problems, the present inventor has further devised a method including: putting a plurality (for example, 20) of cyprinodonts 4e into the water tank for fish 4d; photographing the cyprinodonts 4e by means of the CCD video camera 1 in a direction of bird's-eye to output data; and analyzing the data with the image processing device 1b.

Cyprinodonts belong to fish that lives in a group, and must be under stress if only one cyprinodont lives. The present inventor have understood that the stress have caused the problem, that is, the one cyprinodont 4e has died young in about one month.

More important, it has been proven that cyprinodonts do not take the nose-raising action at 0.2 [ppm] of potassium cyanide but take the nose-raising action at 2 [ppm] of potassium cyanide.

FIG. 18 (Table 5) shows the test data related thereto.

In this connection, the inventor understands the followings. That is, the Water Supply Law clearly recites that allowance of potassium cyanide is 0.01 [mg/L]. It is also asked for issuing an alarm at this low concentration. This is, however, impossible according to analysis of the nose-raising action.

Figure 11:
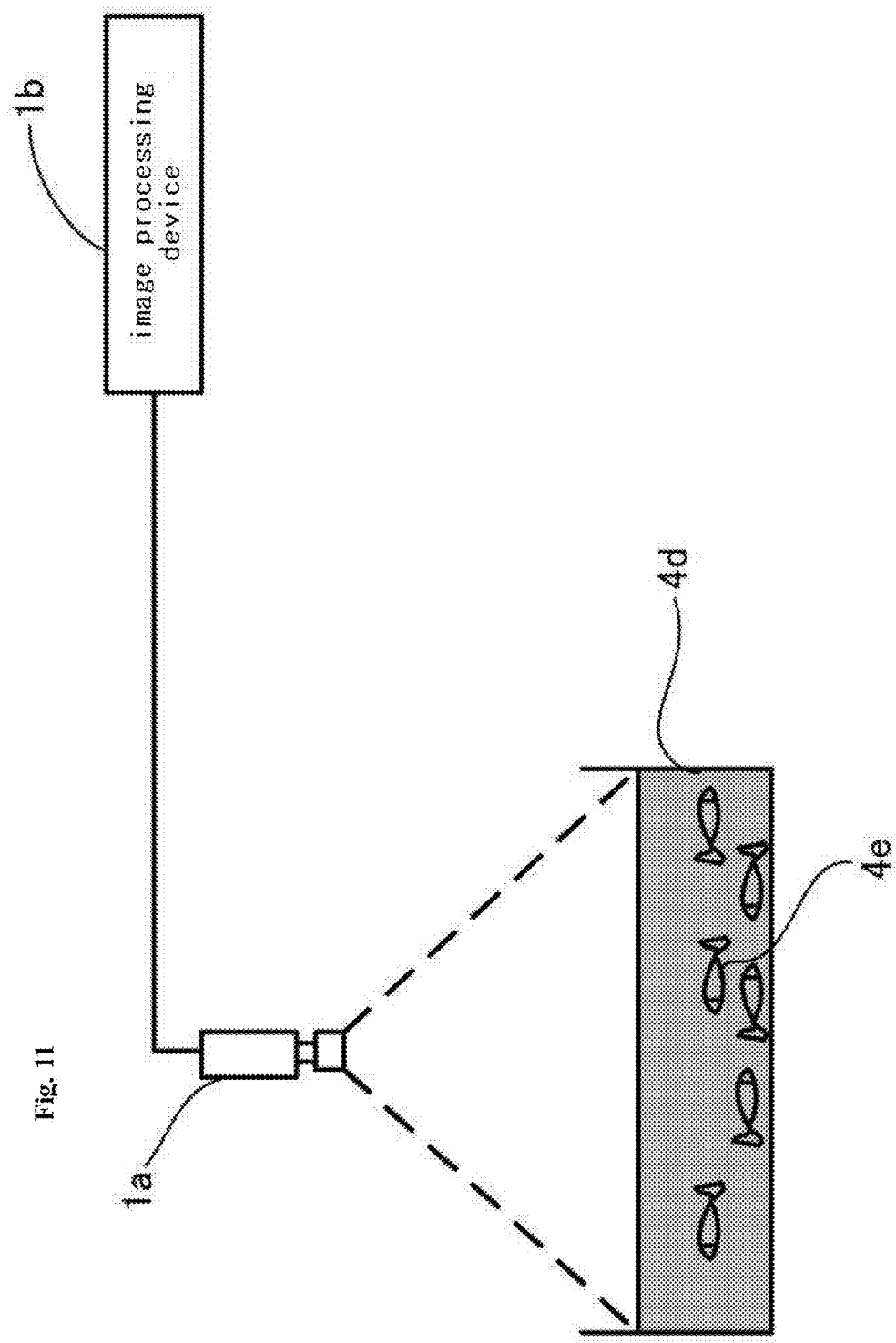
FIG. 11 shows a bird's-eye photographing system.

In order to solve the problem of photographing one cyprinodont from the side wall, the inventor has performed: changing the side photographing system shown in FIG. 10 to the bird's-eye photographing system shown in FIG. 11; using the more (about 20) cyprinodonts; and developing new algorithm. In this way, the present inventor has solved the problem in recent years.

As mentioned above, cyprinodonts 4e belong to fish that live in a rice field for culturing rice. The present inventor has further devised the followings. That is:

making a depth of water within the water tank shallow to be 5 through 8 [cm] as the same as the rice field;

generating water flows by means of the underwater pump 4c; and rearing the cyprinodonts 4e in a group of about 20.

Due to this, the cyprinodonts 4e can live for a long period of time.

Under the low concentration of toxic substances (for example, 0.01 [mg/L] of potassium cyanide), the cyprinodonts 4e do not take at least one of the nose-raising action, the madly-rushing action, the repelling action, and the halt reaction but the cyprinodonts form a fixed group that does not move. The present inventor has discovered the above in recent years.

Figure 12:
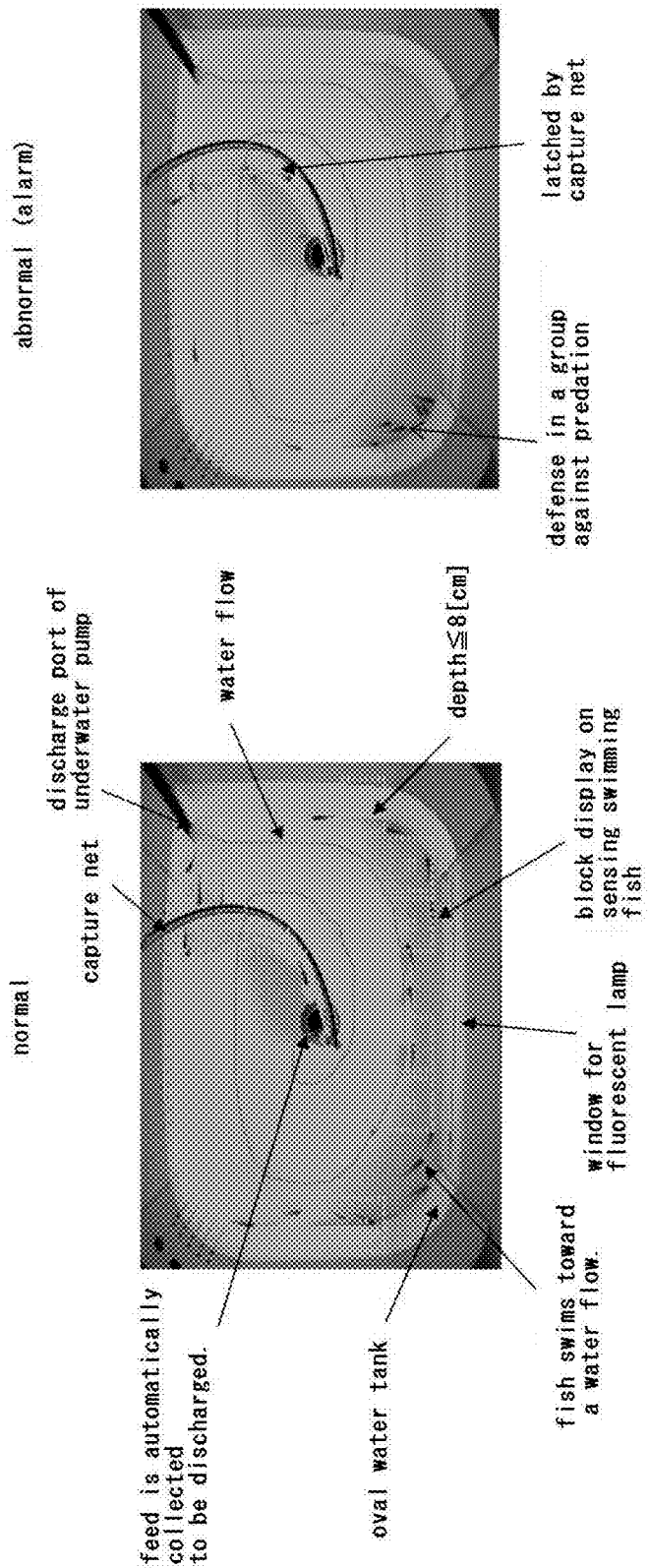
FIG. 12 is a photograph showing the water tank for fish when cyprinodonts are latched by a capture net.

A left photograph in FIG. 12 shows a first state of normal cyprinodonts.

Whereas, under a relatively high concentration of toxic substances, the cyprinodonts 4e take at least one of the nose-raising action, the madly-rushing action, the repelling action, and the halt reaction.

As shown in a right photograph therein, a certain cyprinodont is carried away by water flowing within the water tank for fish 4d. The certain cyprinodont does not die, but swims weakly toward a water flow to be carried away, thereby being latched by the capture net 4f. In other words, it is clear that the capture net 4f can distinguish cyprinodonts strongly swimming from the weakened certain cyprinodont.

Figure 13:
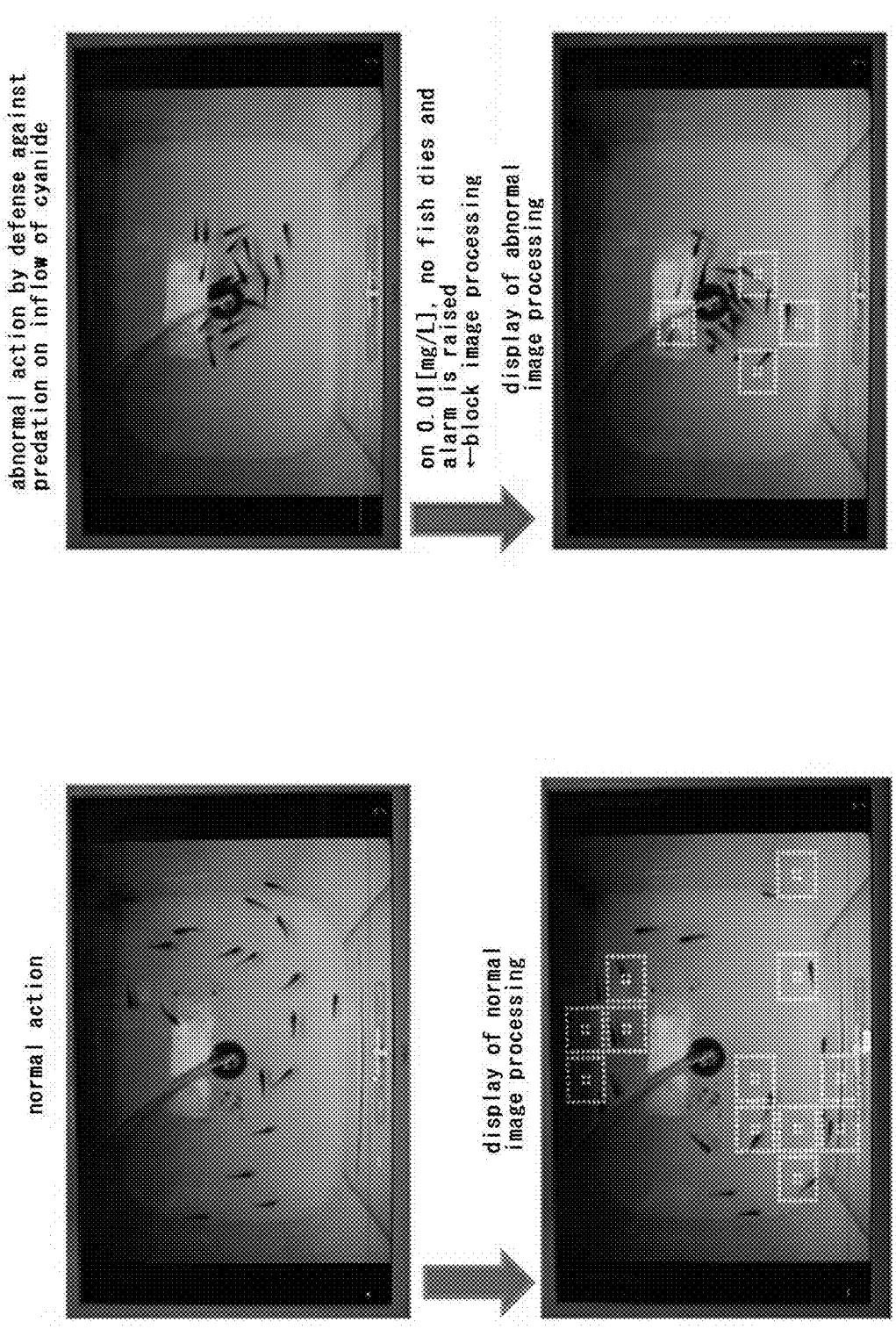
FIG. 13 is a photograph showing a state where the cyprinodonts form a fixed group that does not move upon an alarm with respect to 0.01 [mg/L] of potassium cyanide having been issued.
Figures 14, 15:
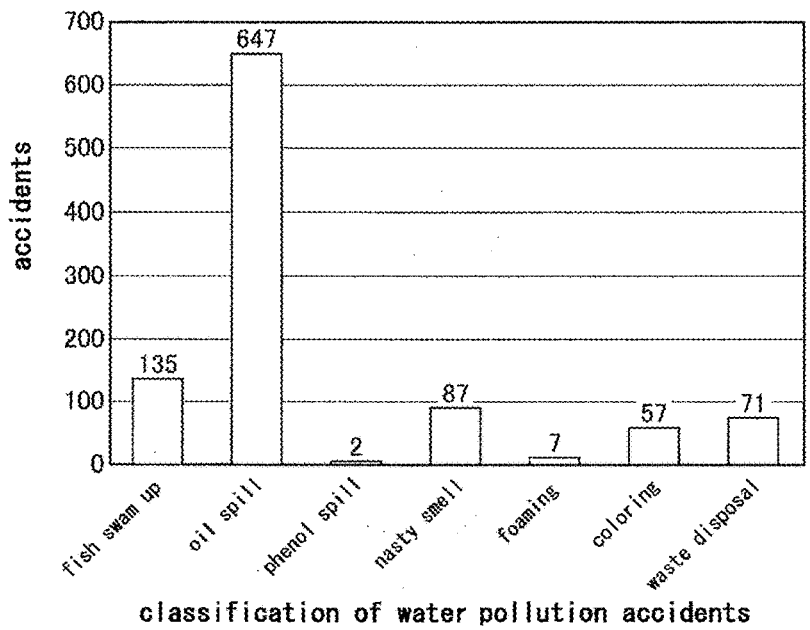
FIG. 14 is a classification table of water pollution accidents (Table 1)
FIG. 15 is a table showing a setting example for defining a number of blocks to be sensed within a predetermined time, and issuing an alarm when the defined numbers of blocks are not sensed within the predetermined time (Table 2)

As shown in a right photograph of FIG. 13, the present inventor has discovered that the cyprinodonts 4e form a fixed group that does not move when the low concentration (0.01 [mg/L]) of potassium cyanide has been exposed thereto (in the test, 5 through 10 hours after that). Furthermore, the present inventor has developed algorithm of issuing an alarm in this state.

As mentioned above, image processing at this time is performed as follows. 56 blocks in total (vertically 7 blocks and horizontally 8 blocks) are arranged onto the entire surface of the water tank for fish 4d; sensing dots for every block of the 56 blocks are configured with 64 sensing dots (vertically 8 sensing dots and horizontally 8 sensing dots). Upon at least one of the plurality of cyprinodonts touching with at least one of the 64 sensing dots, a block to which the touched at least one of the 64 sensing dots belongs is counted.

Algorithm of issuing an automatic alarm is configured according to a system of: defining a number of blocks to be sensed within a predetermined time; and issuing an alarm when the defined numbers of blocks are not sensed within the predetermined time. In addition to the above, new algorithm regarding setting up sensitivity and numbers of sensing dots, and so on has further been developed.

FIG. 19 (Table 6) shows the numbers of blocks and timer setting used herein.

5 [cm] of the lower limit water level of the odor-sensing water tank 4a is also the least operable level of the underwater pump 4c for preventing from empty operation accidents related thereto.

For example, if the water level is not greater than 5 [cm], the underwater pump 4c falls into the empty operations, gears of the underwater pump are overheated to stop rotation thereof.

Since 5 [cm] of the lower limit water level is maintained, the underwater pump 4c keeps operation thereof, for example, even if the water supply of the raw water from the water inlet 4n has been stopped. So, the water within the water tank for fish 4d also keeps flowing so that the group of cyprinodonts can live therein.

The raw water passes through the meshes of the capture net 4f. The meshes are configured smaller than the cyprinodonts 4e. So, the cyprinodonts 4e cannot pass through the meshes of the capture net 4f.

As mentioned above, the cyprinodonts have habit of swimming toward a water flow circulating within the water tank for fish 4d.

When about 2 [ppm] concentration of potassium cyanide is contained in the raw water, the cyprinodonts 4e swim weakly toward a water flow to be carried away, thereby being latched by the capture net 4f.

According to the present invention, although the nose raising-action cannot be specified, it can distinguish cyprinodonts affected by toxic substances from and cyprinodonts acting normally.

When 2 [ppm] of potassium cyanide is contained, half of the cyprinodonts 4e will die within 24 hours. Immediately after a certain cyprinodont 4e has been latched by the capture net 4f, the certain cyprinodont 4e is not dead. Water pressure of water flows forces the certain cyprinodont 4e on the capture net 4f so that the certain cyprinodont 4e cannot escape from the capture net 4f, thereby keeping latched thereon. In this way, the latched certain cyprinodont is distinguished from acting cyprinodonts.

The group of cyprinodonts within the water tank for fish 4d are classified into at least one of latched cyprinodonts and acting cyprinodonts. Image processing in this Embodiment analyzes the number of the acting cyprinodonts.

The greater number of the latched cyprinodonts increases, the less number of the acting cyprinodonts decreases. Reflecting the fact, alarms will be issued in a stepwise manner.

When the number of the acting cyprinodonts has decreased gradually, alarms are issued also in the stepwise manner, which is a different phenomenon from that of decreasing acting numbers caused by illness and/or life span which are/is special to cyprinodonts. For this reason, it is judged that toxic substances are contained within the raw water, thereby issuing the alarms.

Next, the overall system of the automatic water quality surveillance apparatus in Embodiment 1 will now be explained briefly.

About 1.5 [L/m] of the raw water is supplied to the odor-sensing water tank 4a to be discharged by the underwater pump 4c to the inner wall surface of the water tank for fish 4d.

A group of (about 20) cyprinodonts are reared by water tank for fish 4d for a long period of time.

The number of acting cyprinodonts is successively analyzed by means of the image processing device 1b all day long, thereby surveying toxic substances contained in the raw water.

The group of cyprinodonts are always exposed by fresh raw water by draining the same amount of the raw water as that of newly supplied raw water into the water tank for fish 4d. For example, if the toxic substances are contained in the raw water, alarms are automatically issued in a stepwise manner according to the decreased number of acting cyprinodonts.

The alarms issued in the stepwise manner include four steps of: "Caution_level 1"; "Caution_level 2"; "Caution_level 3"; and "Abnormal."

In a case where: the toxic substances are contained in the raw water; and the number of acting cyprinodonts is decreased from about 20 to be zero or nearly zero, the state is judged to issue a heavy alarm of "Abnormal."

At this time, in order to use the raw water of the water tank for fish 4d as inspection water, the solenoid valve 4h is opened to automatically store the inspection water within the water-sampling container 4i. In addition, the state is informed to the manager by turning on and off an "Abnormal" lamp on the display panel 1d, sounding a buzzer, and/or outputting signals to the outside.

The feeder 4j electrically feeds the group of cyprinodonts within the water tank for fish 4d once or twice for every day.

The CCD video camera 1a photographs the group of cyprinodonts within the water tank for fish 4d. In addition, in order to improve photographing effect thereby, the small 5 [W] of fluorescent lamp 4g is continuously turned on all day long.

The small 5 [W] of fluorescent lamp 4g controls photosynthesis, thereby the development of algae within the water tank for fish 4d can be suppressed.

The CCD video camera 1a photographs the group of cyprinodonts 4e within the water tank for fish 4d all day long, image signals thereof are entered into the peripheral control unit 1c to divide one image included in the image signals into the same four images to be entered into the image processing device 1b.

Figure 16:
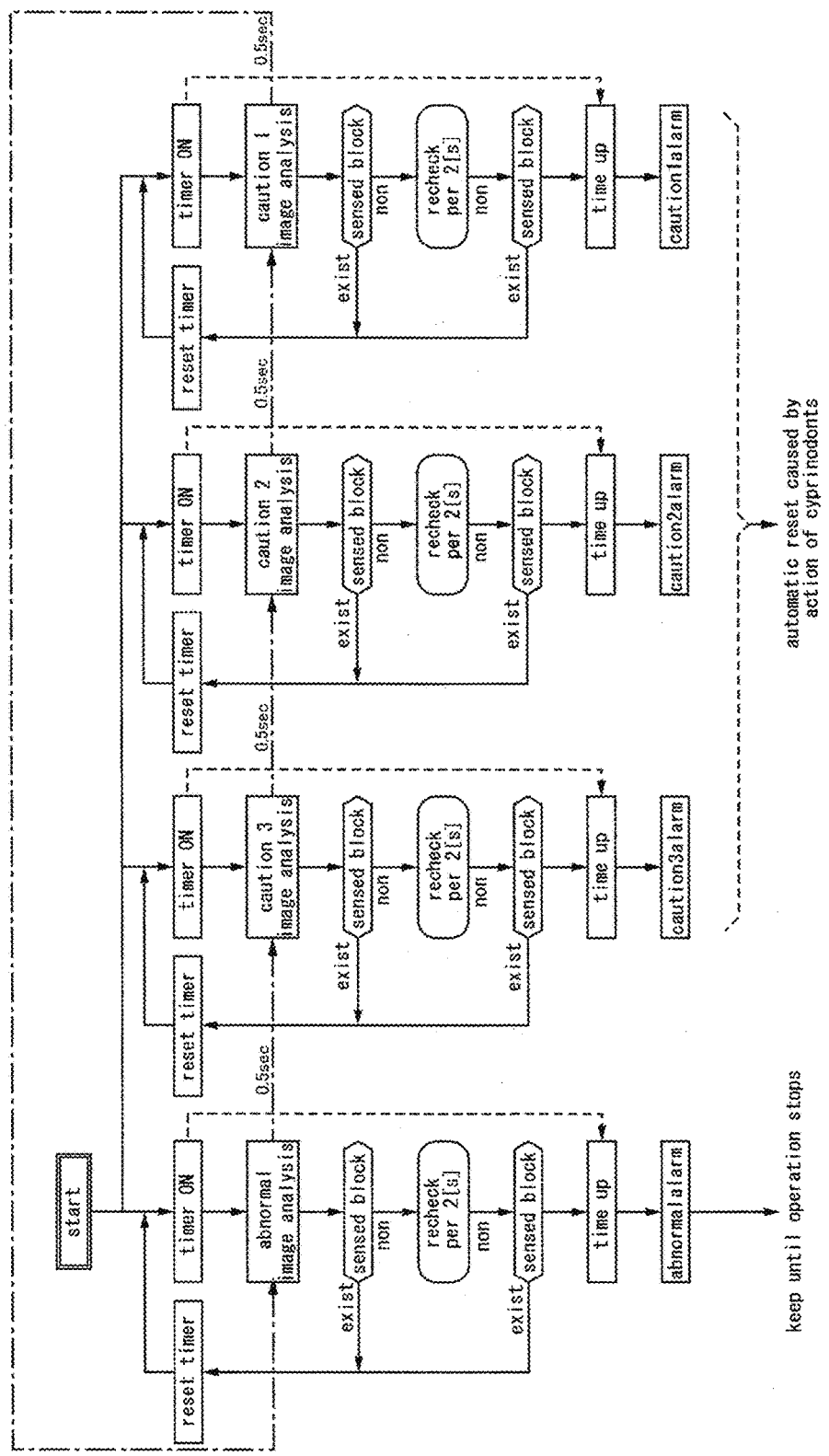
FIG. 16 is a table showing surveillance flows (Table 3)

As shown in FIG. 16 (Table 3), the image processing device 1b sequentially analyze the four images, needs a half of a second for analyzing one image, and further needs two seconds for completing the analysis of all of the four images.

The analyzing method is performed as follows:
entering images at intervals of ¼ second;
making the current image and the next image overlap each other; and
capturing action of the cyprinodonts by means of the 56 blocks arranged onto the entire surface of each of the images,
wherein:
each of the 56 blocks is composed of 64 sensing dots (vertically 8 sensing dots and horizontally 8 sensing dots);
the 56 blocks in total (vertically 7 blocks and horizontally 8 blocks) are arranged onto the entire surface of each of the images; and
upon at least one of the plurality of cyprinodonts swimming to be sensed by at least one of the 64 sensing dots, a block to which the sensed at least one of the 64 sensing dots belongs is counted.

The sensing is performed as follows: the action of the cyprinodonts is defined using digital values of a change of concentration of every sensing dot; the defined digital values are measured; and it is judged to be sensed when concentration difference not less than a predetermined threshold is detected.

The number of blocks touched by at least one of the cyprinodonts is analyzed. With respect to the four steps of "Caution_level 1", "Caution_level 2", "Caution_level 3", and "Abnormal", the respective block number for the four images has been predetermined. When the analyzed number of blocks is less than the predetermined respective block number, an alarm with respect to the four steps of "Caution_level 1", "Caution_level 2", "Caution_level 3", and "Abnormal" is issued.

For example, a first value of "0" for one image may be set up so as to indicate "Abnormal." When the analyzed value of a certain image is equal to "0" actually, it is shown that no cyprinodont moves within the 56 blocks divided from the entire surface of the certain image.

Accordingly in this case, alarm output of the certain image should be "Abnormal."

If the first value of "0" has been once judged in the first two seconds, whether or not no cyprinodont acts actually should be confirmed.

For this reason, a predetermined time is set up with setting by means of a timer to provide with a function for confirmation.

For example, the predetermined time may be set up to be 20 [s]. In this case, only if the first value of "0" has been confirmed 10 times repeatedly, a final "Abnormal" alarm should be issued.

The above confirmation function enables to issue reliable alarms.

For example, the setting may be made by setting up: a fourth value of "7" for "Caution_level 1"; a third value of "5" for "Caution_level 2"; a second value of "3" for "Caution_level 3"; and the first value of "0" for "Abnormal." Such setting enables to automatically issue alarms in the stepwise manner according to the decreased number of acting cyprinodonts belonging to the group.

According to the alarms in the stepwise manner, effect can be obtained, the effect enabling water examiners to cope with a task beforehand.

The display panel 1d displays prior alarm information of "Caution_level 1", "Caution_level 2," and "Caution_level 3" and serious alarm information of "Abnormal" thereon. The monitor television 1e displays the cyprinodonts 4e within the water tank for fish 4d and the blocks obtained by the image processing in a superimposed manner.

Functions of the image processing device 1b and action of the cyprinodonts 4e can be confirmed by watching the screen of the monitor television 1e. The alarms of the four steps are outputted to the outside from an external output port.

The action analysis of the cyprinodonts 4e is performed by the image processing device 1b without connecting the same to the personal computer 2i.

A CPU thereon running a program for a logic circuit board has been mounted onto the image processing device 1b. The image processing device 1b is not affected by an OS (operating system) which is regularly updated by computer software makers, is stable for a long time, and can be easily operated by any one using exclusive three buttons.

The display panel 1d further displays device alarm information including items of: leakage; water level abnormality; turning fluorescent-lamp off; and so on other than the alarms with respect to water quality.

The leakage information is generated by sensing leakage with the leakage sensor 1g of a leakage pad. The water level abnormality information is generated by sensing the water level with the water level sensor 3c attached to the odor-sensing water tank 4a. And, the turning fluorescent-lamp off information is generated by sensing the turning fluorescent-lamp off with an electrical connection sensor.

The water level sensor 3c is installed at a lower portion of the water level-adjusting pipe. The device alarm information also can be outputted to the outside from the external output port.

In Embodiment 1 according to the present invention, the CCD video camera 1a photographs the water tank for fish 4d in a direction of bird's-eye. As shown in FIG. 1, the electronic part is arranged at an upper portion, and the raw water circulation part is arranged at a lower portion, respectively.

Due to this, width dimensions can be reduced so that the housing of the apparatus can be downsized. All necessary devices can be stored within the housing to form a small self-supporting shape, thereby freely selecting an installation space thereof. In other words, the apparatus can be installed anywhere.

Next, automatic contamination sensing an oily odor, a mold odor, or the like by means of an odor sensor will now be explained. The odor sensor includes: the odor sensor sensing element 3; and the odor sensor control unit 2 connected to the odor sensor sensing element 3 by the cable 3g.

As mentioned above in this Embodiment 1, within the water tank for fish 4d in the surveillance water tank 4 of existing automatic water quality surveillance apparatus 1, which has been already commercially produced to be delivered in the future, or which has been already commercially produced and also have been delivered, the about 20 cyprinodonts 4e always and continuously are reared.

The water tank for fish 4d always and continuously receives raw water including: river flowing water; lake water; and ground water. The CCD video camera 1a photographs abnormal behavior when the raw water contains toxic substances therein, the abnormal behavior including: the first case where the plurality of cyprinodonts 4e form a fixed group that does not move; the second case where the plurality of cyprinodonts 4e take at least one of repelling action and madly-rushing action; and the third case where the plurality of cyprinodonts die.

The digital conversion on the image signals therefrom is performed, and an abnormality according to the image processing is judged to automatically output an alarm.

The odor sensor is further provided for the above apparatus, thereby enabling to automatically sense not only contamination by the toxic substances but also an odor such as an oily odor, a mold odor, or the like.

Utilizing the above apparatus, the water examiners can automatically sense almost all of the water pollution accidents mentioned at the beginning of the specification, and can cope with an initial task, thereby preventing from serious water pollution accidents. In this way, life and health of the inhabitants can be protected.

When cyprinodonts, fathead minnows, zebra fish, daphnias of invertebrates, crustaceans within the water tank for fish 4d constituting the surveillance water tank 4 in the above-mentioned automatic water quality surveillance apparatus 1 with fish are exposed to geosmin and/or 2-MIB (2-methyliso borneol), which are/is a small amount of several kind of oil and/or mold odor substances, the fish reared within the water tank for fish 4d is observed neither to be damaged nor to be injured caused by the pollution. This is because the oil keeps floating on a water surface thereof.

In addition, geosmin of mold odor substances and 2-MIB (2-methyliso borneol) hardly affect the fish. In this context, the present inventor has confirmed according to tests that the conventional automatic water quality surveillance apparatus with fish cannot sense the oil and/or the mold odor substances based on abnormal behavior of the fish.

Exsisting apparatuses have been merchandised according to: the relative permittivity method of sensing floating oil as the oil film; the beam reflection method of irradiating light to a water surface so as to measure reflected light therefrom; and so on.

All apparatuses related to the above have too large size. In the market, there is no apparatus capable of being implemented into the automatic water quality surveillance apparatus with fish. A handy type of oil-measuring instrument can be only considerable for the same. It is, however, difficult to adapt the instrument since the instrument is not designed to be used continuously for a long period of time, and does not include a function of outputting an alarm to the outside.

A disclosed method for sensing mold odor substances contained in raw water, including:
preparing the raw water so as to contain contaminants of a fixed pH;
adding CD derivative as a sensor into the prepared raw water, the CD derivative including at least one of the following (I) through (V):
(I): 3-deoxy-3-(6-hydroxy-2-naphthamide)-βCD;
(II): 3-deoxy-3-(3-hydroxy-2-naphthamide)-βCD;
(III): 3-deoxy-3-(3-hydroxy-2-naphthamide)-γCD;
(IV): 3-deoxy-3-(6-hydroxy-1-naphthamide)-γCD; and
(V): 3-deoxy-3-(2-hydroxy-1-naphthamide)-αCD;
irradiating ultraviolet light to the added raw water; and
measuring fluorescence intensity in a specific wavelength, thereby sensing and specifying pollution.

However, no practical example of the above is found. In fact, users of the city water and/or water examiners related thereto smell with their nose for sensing.

In view of the above, the automatic water quality surveillance apparatus with fish in this Embodiment 1 is provided with the odor sensor including: the odor sensor sensing element 3; and the odor sensor control unit 2 connected to the odor sensor sensing element 3 by the cable 3g so as to solve the above problems.

That is, the odor sensor in this Embodiment 1 is provided with: the odor sensor sensing element 3 made small and lightweight; and the odor sensor control unit 2; the odor sensor sensing element 3 and the odor sensor control unit 2 are separately arranged and are connected to each other by means of the cable 3g.

As shown in FIG. 3, the surveillance water tank 4 of the automatic surveillance apparatus 1 is composed of: the water-receiving tank 4m; the odor-sensing water tank 4a; and the water tank for fish 4d.

The raw water is supplied from the water inlet 4n into the water-receiving tank 4m to be stored therein.

The plurality of supply holes 4o are opened in a step form through the water-receiving tank 4n. So, from the supply holes 4o opened in the step form, the raw water is supplied to the odor-sensing water tank 4a.

The raw water supplied to the odor-sensing water tank 4a is discharged by the underwater pump 4c to the inner wall surface of the water tank for fish 4d.

The odor sensor sensing element 3 is installed at an upper portion of the odor-sensing water tank 4a in the middle of the raw water channel.

Consideration must be taken with respect to where and how the odor-sensing water tank 4a should be installed so as to prevent an event where the odor-sensing water tank 4a is under the raw water or flooded thereby. For example, the odor-sensing water tank 4a may be adhered onto a side surface of the supply hole 4o of the water-receiving tank 4m.

Tests show that the higher oil temperature is, the more easily sensing becomes even in a low concentration.

In order to improve sensing performance of the odor sensor sensing element 3, a heater heating the raw water is provided at a bottom portion of the odor-sensing water tank 4a so as to heat the oil floating on the surface of the raw water, thereby promoting decomposition of the oil. At the same time, the heated water evaporates, and the odor is made stronger. In this way, the sensing performance is promoted.

Next, results of sensing tests regarding the odor sensor according to the present invention will now be recited.

Figure 6:
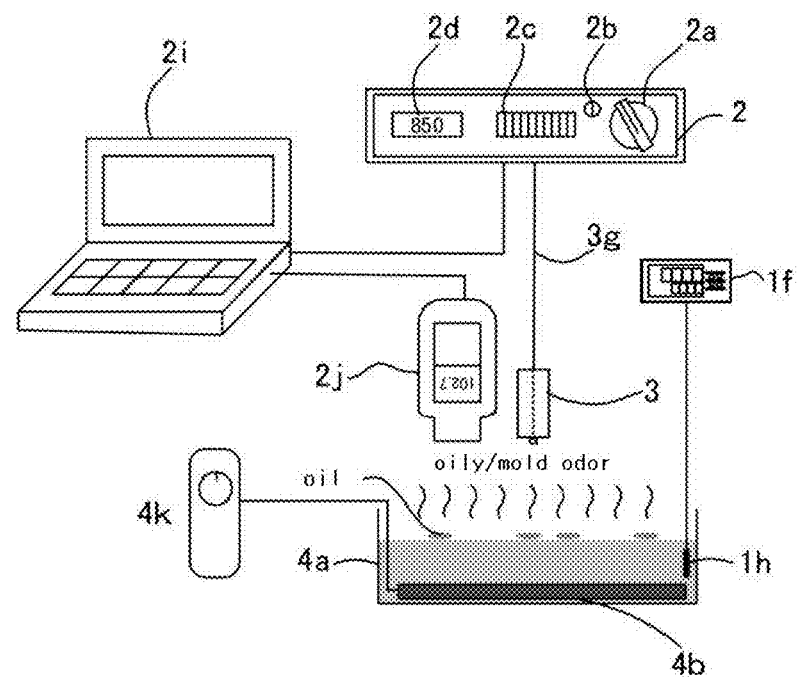
FIG. 6 is a block diagram of a test apparatus used for sensing tests with respect to an oily odor and/or a mold odor in the odor sensor control unit connected by the cable to the odor sensor sensing element of the automatic water quality surveillance apparatus in any one of Embodiments 1 to 2.

Referring to FIG. 6, how to test the sensor is explained.

The raw water has been put into the odor-sensing water tank 4a, the ceramic heater 4b has been sunk at the bottom portion thereof, and the thermostat 4k has set up test temperature. Furthermore, the odor sensor sensing element 3 and the odor sensor control unit 2, which constitute the odor sensor, have been connected to each other by the cable 3g.

As an evaluation device of the odor sensor, a portable VOC (Volatile Organic Compounds) monitor (Name: "Toxira Pro PID," produced by RAESYSTEMS (U.S.A.) and the odor sensor sensing element 3 have been arranged on an upper portion of the odor-sensing water tank 4a side by side.

VOC values [ppm] measured by the evaluation device have been downloaded into the personal computer 2i.

Similarly, sensing values [mV] measured by the odor sensor control unit 2 have been also downloaded into the personal computer 2i.

The personal computer 2i has shown the measurement table whose left vertical axis indicates the sensing values [mV] of the odor sensor, and whose right vertical axis indicates the VOC values [ppm].

First, regarding tests of temperature characteristics of the odor sensor, the raw water has been put into the odor-sensing water tank 4a, the ceramic heater (heater) 4b has been sunk at the bottom portion thereof, and the thermostat 4k has set up test temperature. The sensing performance of the odor sensor has been confirmed based on a change of water temperature.

The oil type has been 1 [mg/L] of light oil. Six steps of temperature of 5 [Centigrade], 15 [Centigrade], 20 [Centigrade], 25 [Centigrade], 30 [Centigrade], and 35 [Centigrade] have been used. And, sensitivity has been set up to "low sensitivity". In this way, measurement has been performed.

Referring to the test table shown in FIG. 20 (Table 7), it is apparent that the sensing performance changes in accordance with temperature difference.

The horizontal axis of the temperature test table indicates time [s]. Measurement has performed from 0 [s] to at most of 300 [s] for every 10 [s].

The left vertical axis indicates the values [mV] measured by the odor sensor. Measurement has performed from 250 [mV] to at most of 500 [mV] using steps of 50 [mV].

When immediately after the test has begun and water temperature has been the least of 5 [Centigrade], the value measured by the odor sensor has been 277 [mV]. And, when the water temperature has been the most of 35 [Centigrade], the value measured by the odor sensor has been 294 [mV].

After 300 [s] from the beginning of the tests and the water temperature has been the least of 5 [Centigrade], the value measured by the odor sensor has been 333 [mV]. And, when the water temperature has been the most of 35 [Centigrade], the value measured by the odor sensor has been 482 [mV].

Figure 21:
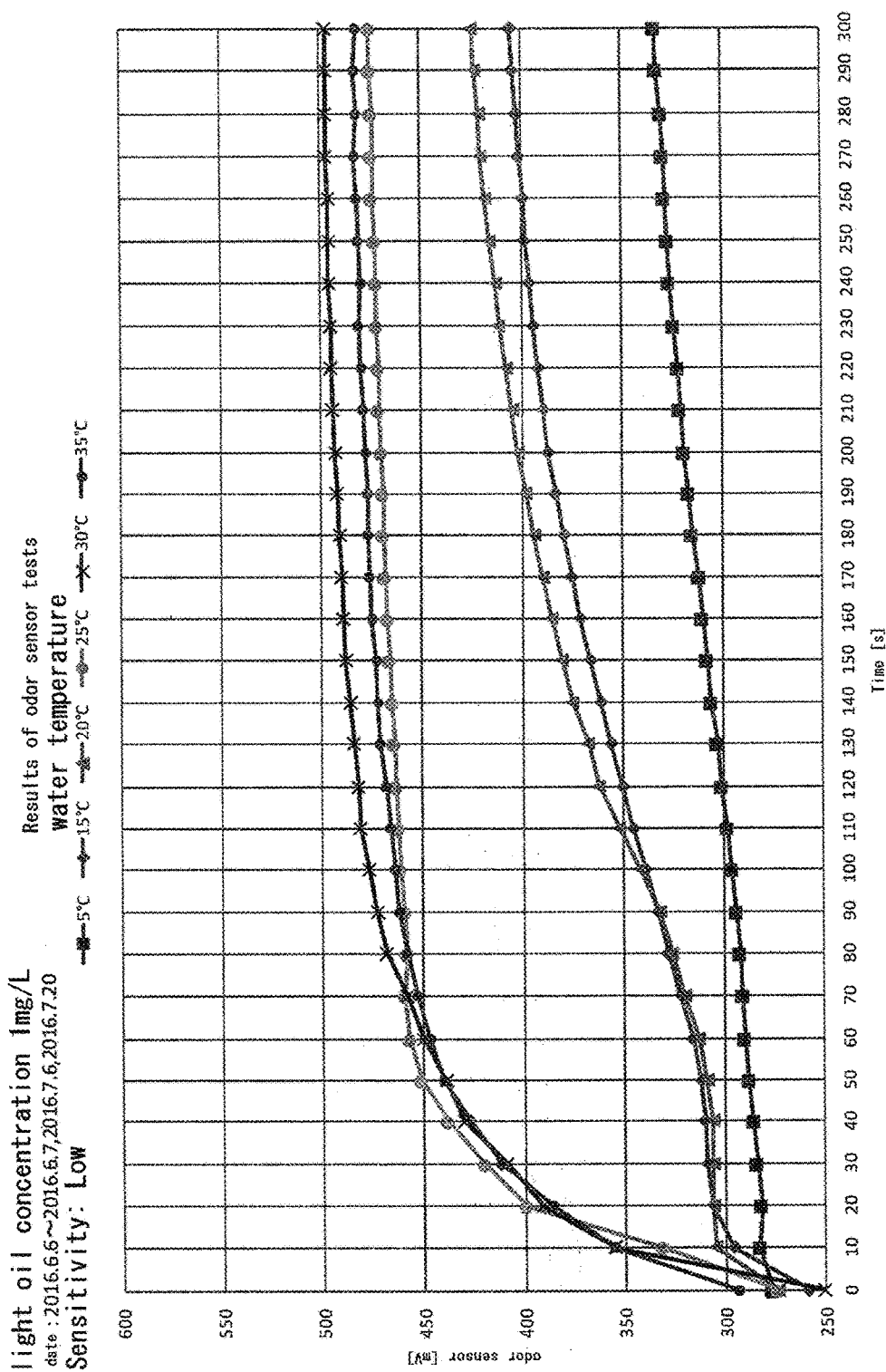
FIG. 21 is a graph of the measured values of Table 7 (Table 8)
Figure 23:
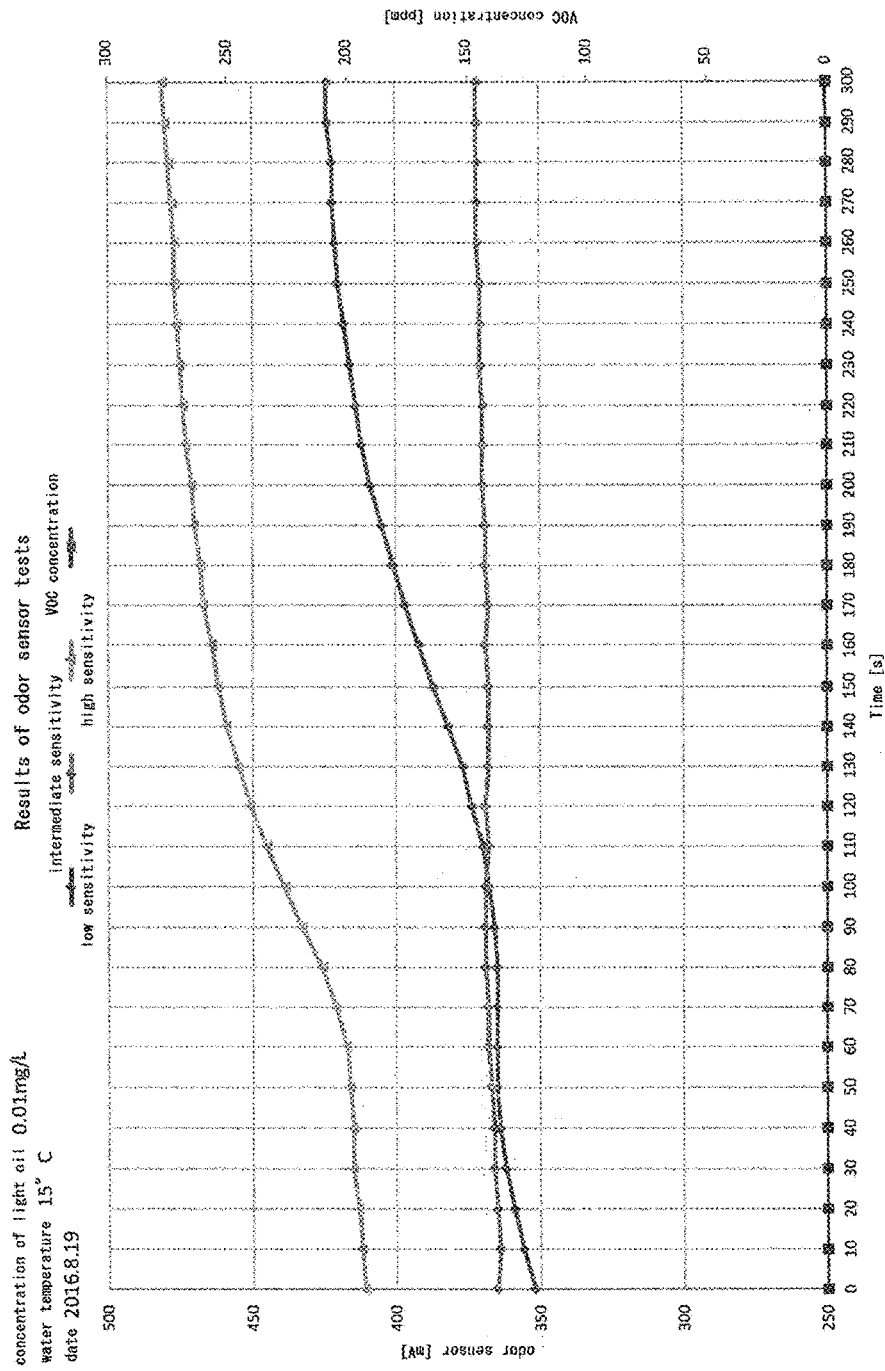
FIG. 23 shows results of odor sensor tests (Table 10)
Figure 24:
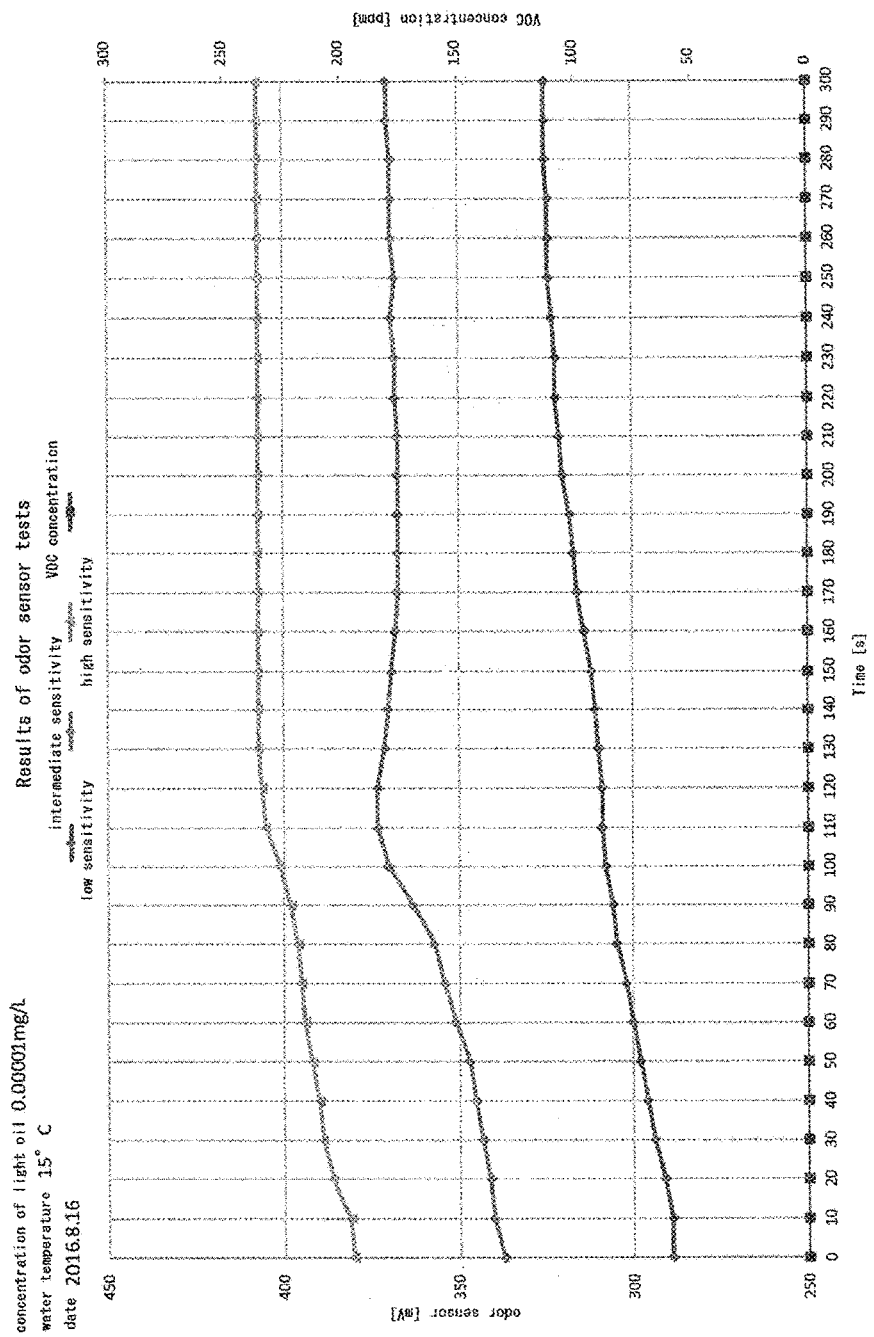
FIG. 24 shows results of odor sensor tests (Table 11)
Figure 25:
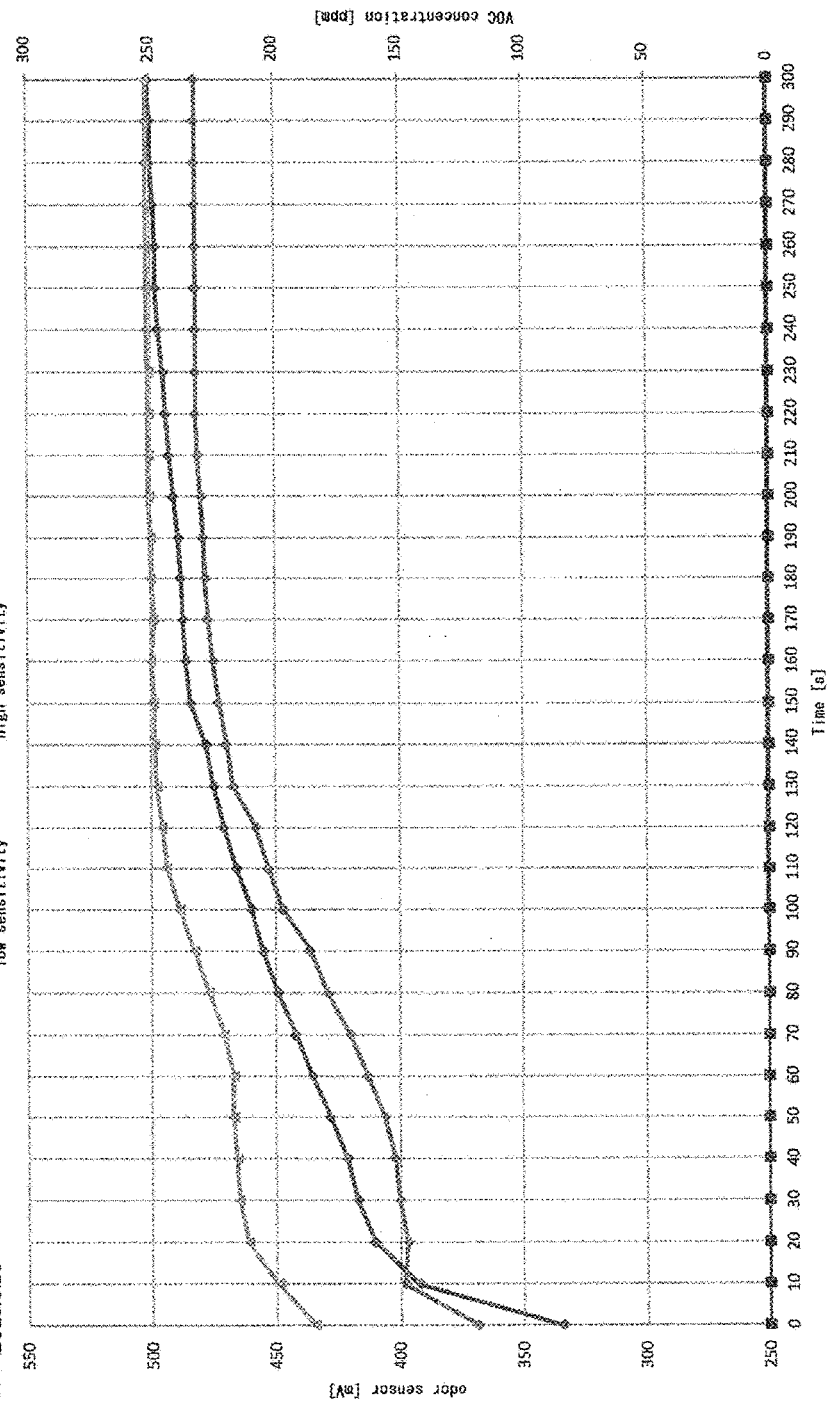
FIG. 25 shows results of odor sensor tests (Table 12)
Figure 26:
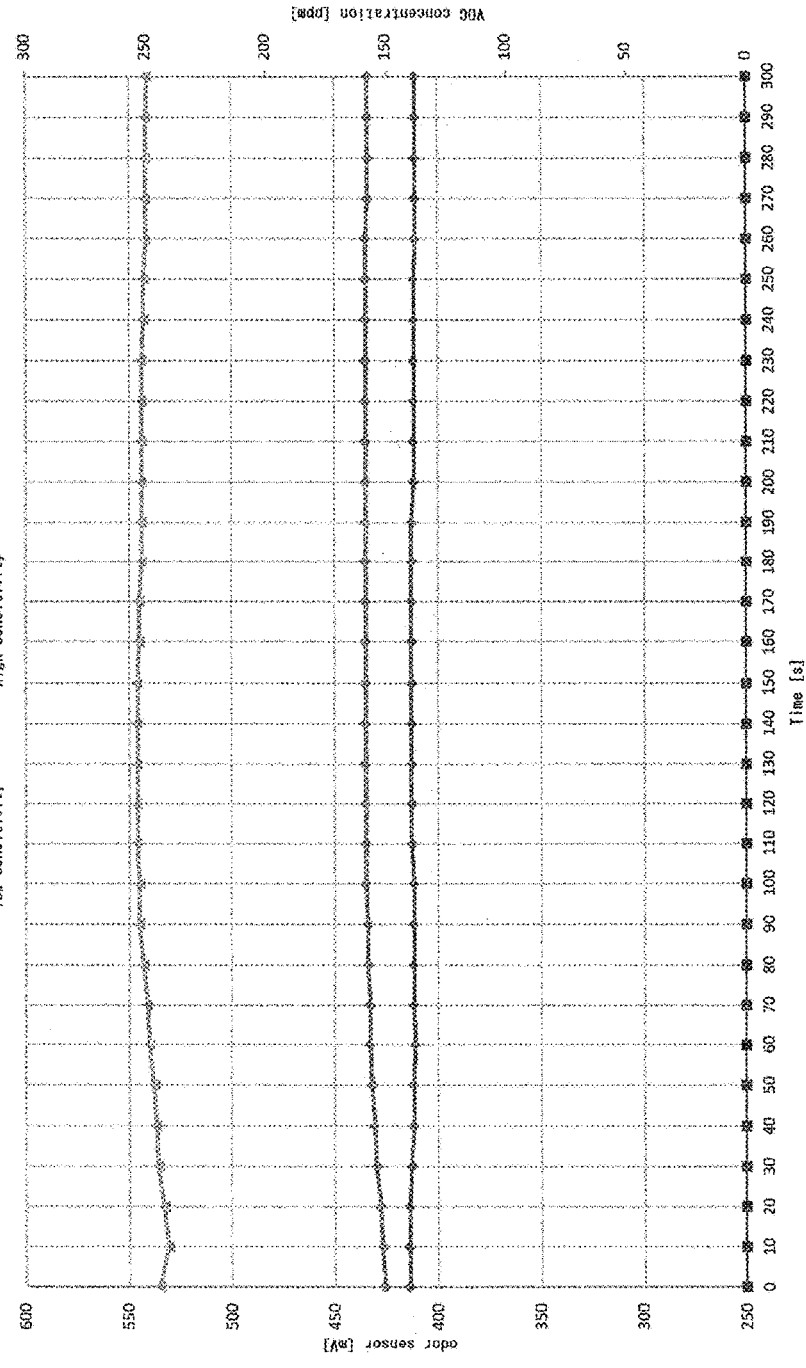
FIG. 26 shows results of odor sensor tests (Table 13)
Figure 27:
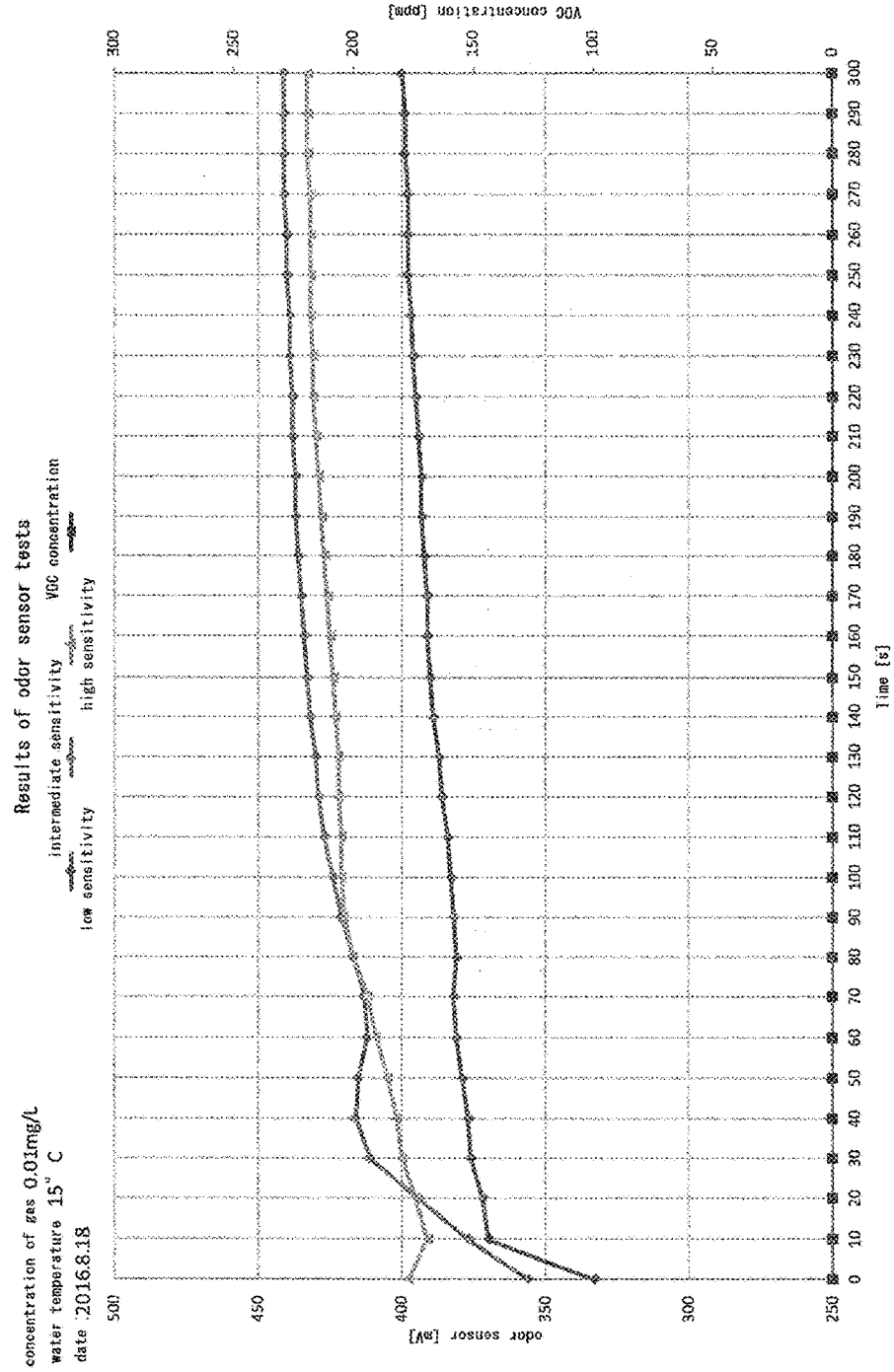
FIG. 27 shows results of odor sensor tests (Table 14)
Figure 28:
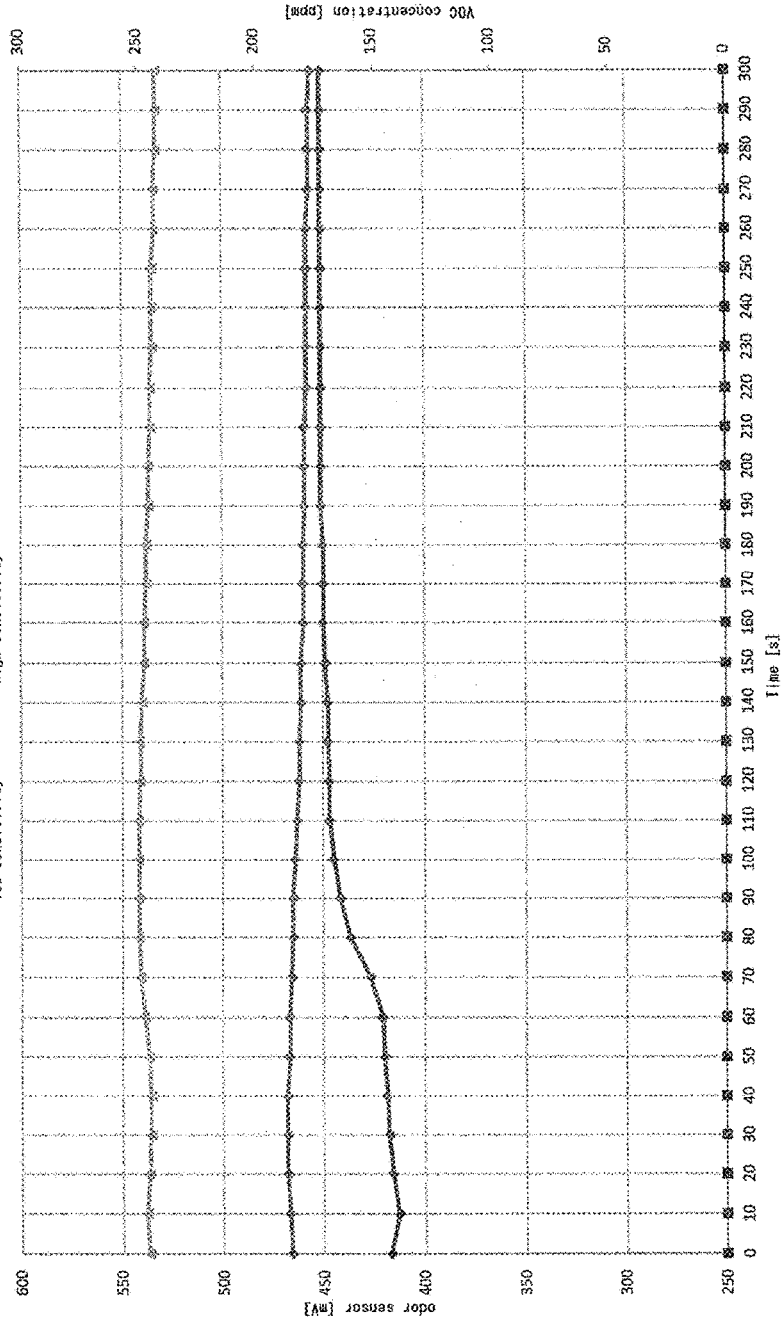
FIG. 28 shows results of odor sensor tests (Table 15)
Figure 29:
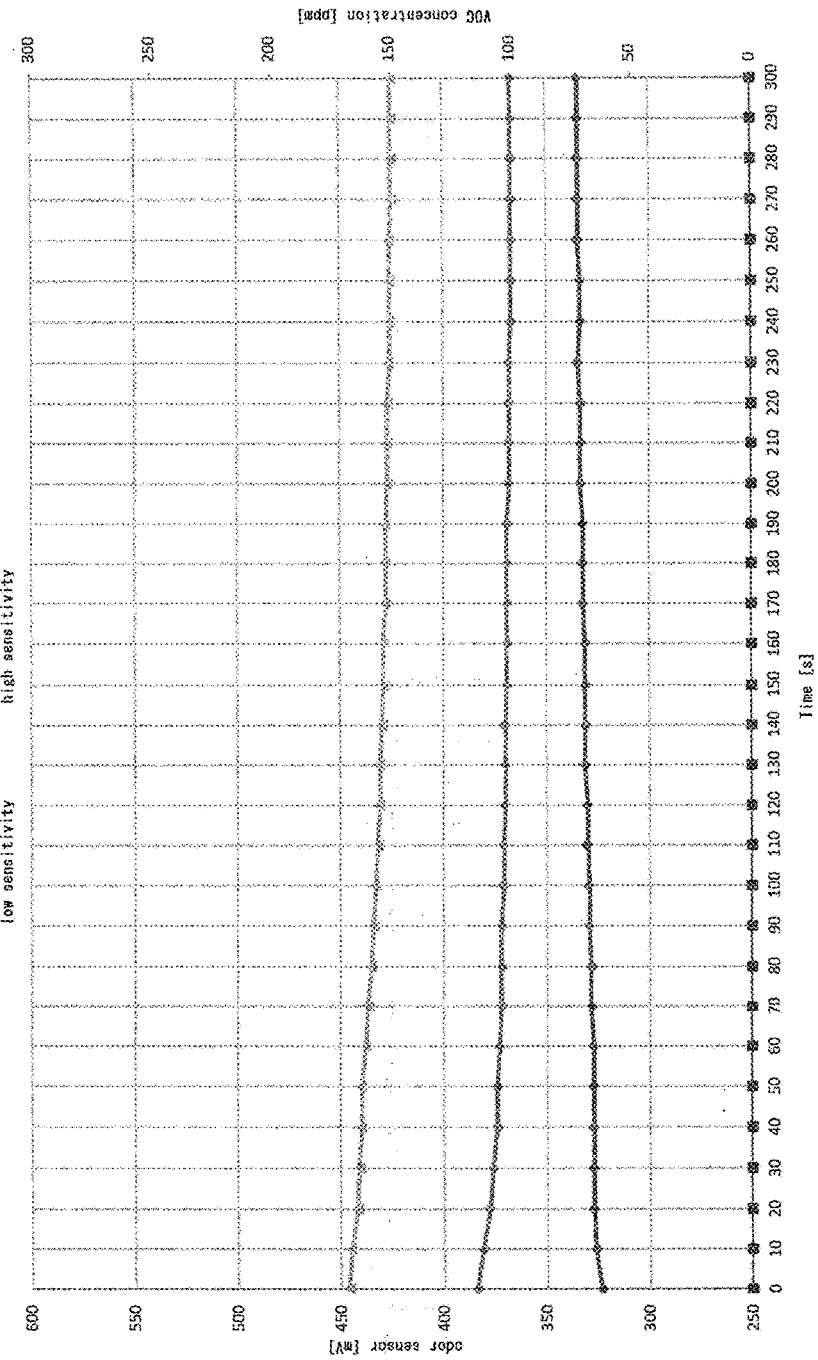
FIG. 29 shows results of odor sensor tests (Table 16)
Figure 30:
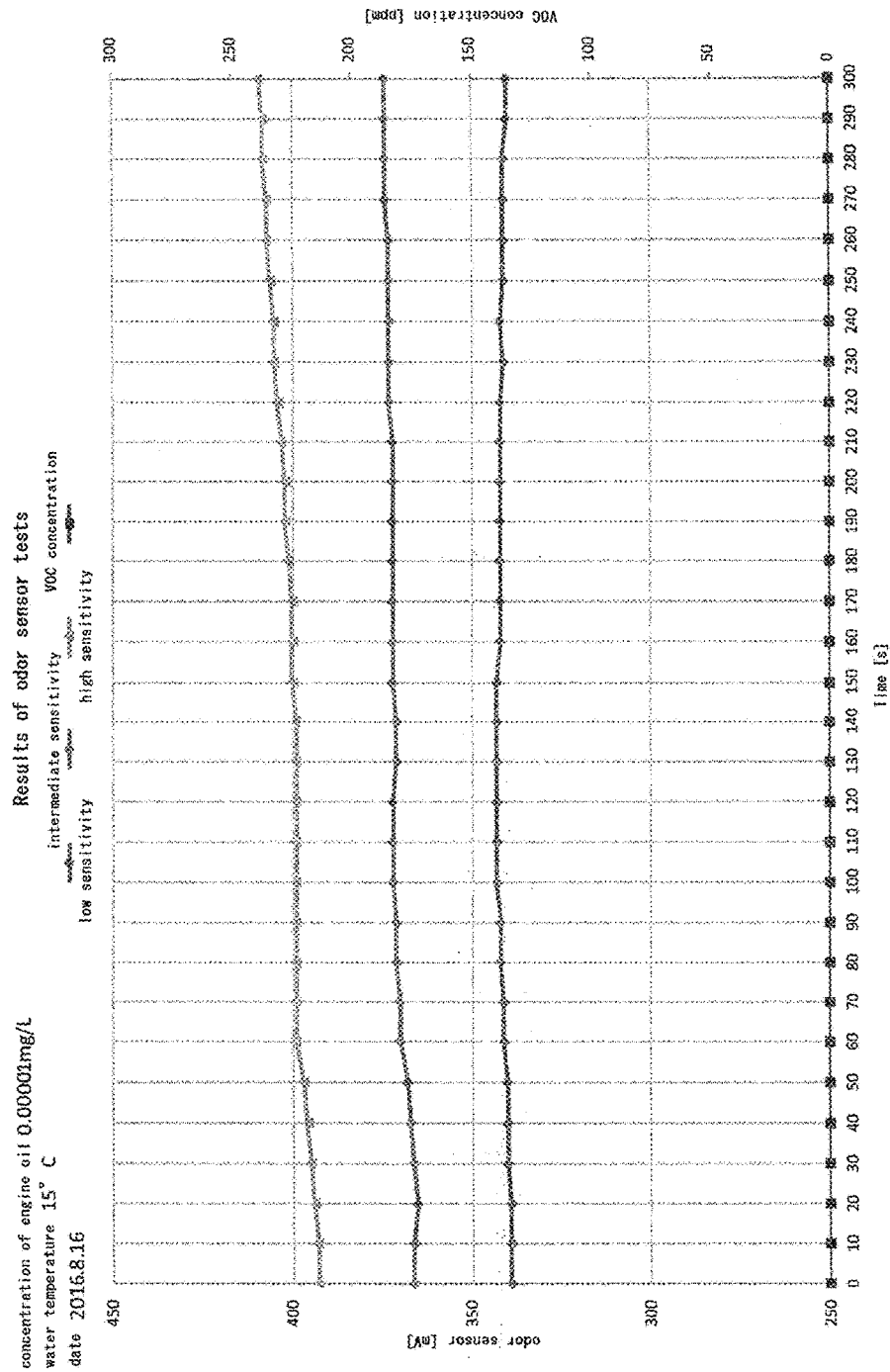
FIG. 30 shows results of odor sensor tests (Table 17)
Figure 31:
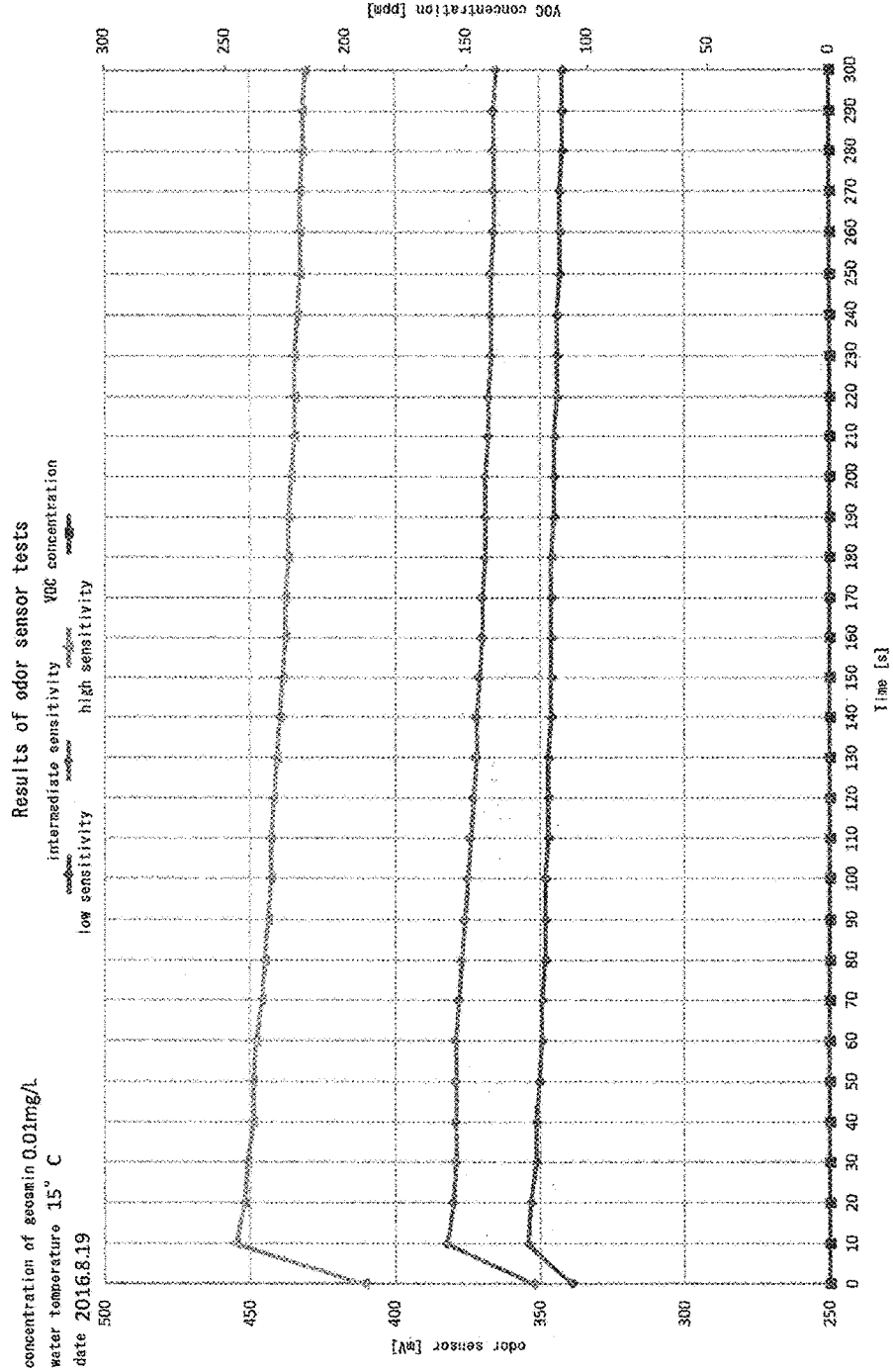
FIG. 31 shows results of odor sensor tests (Table 18)
Figure 32:
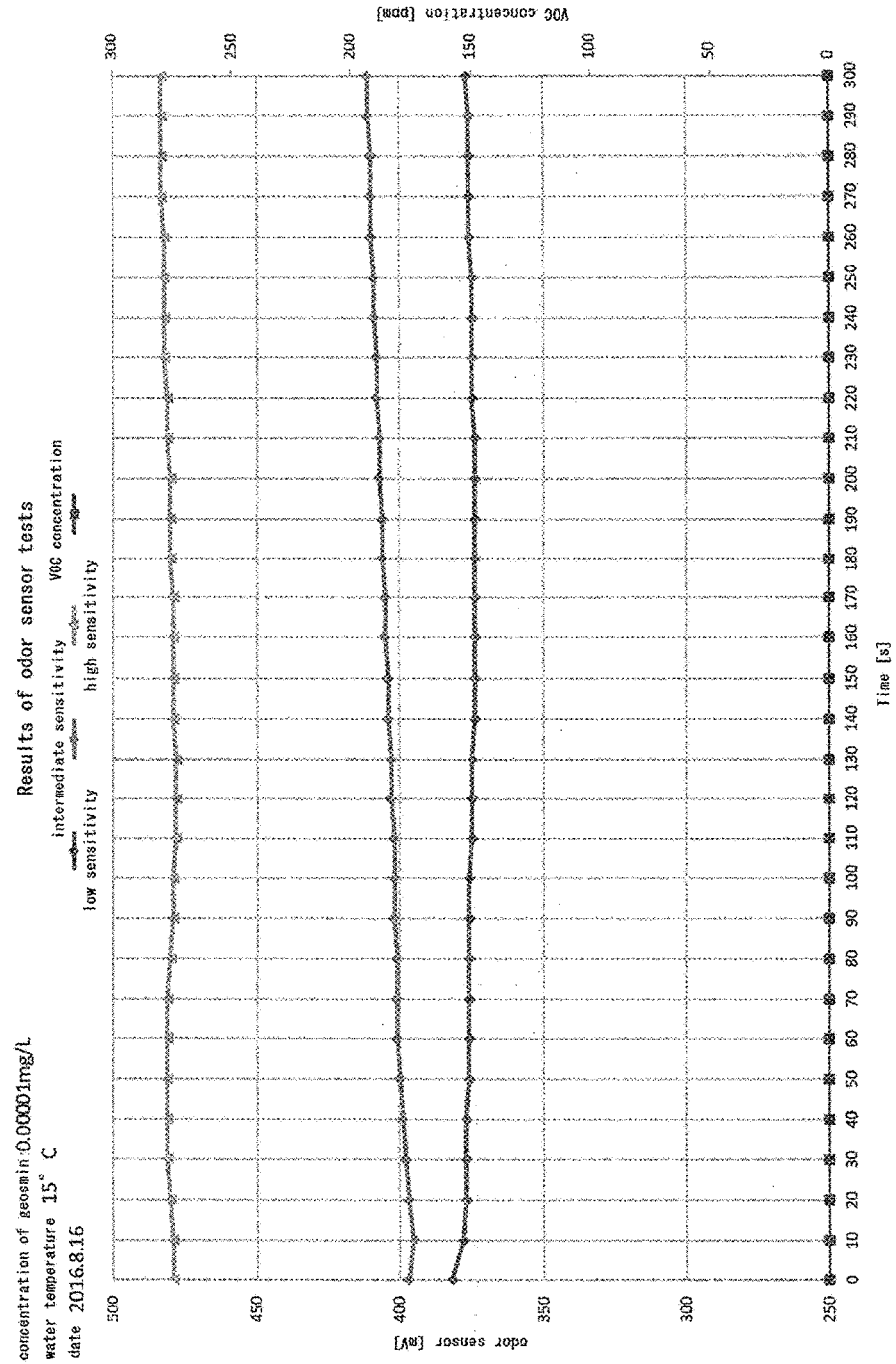
FIG. 32 shows results of odor sensor tests (Table 19)
Figure 33:
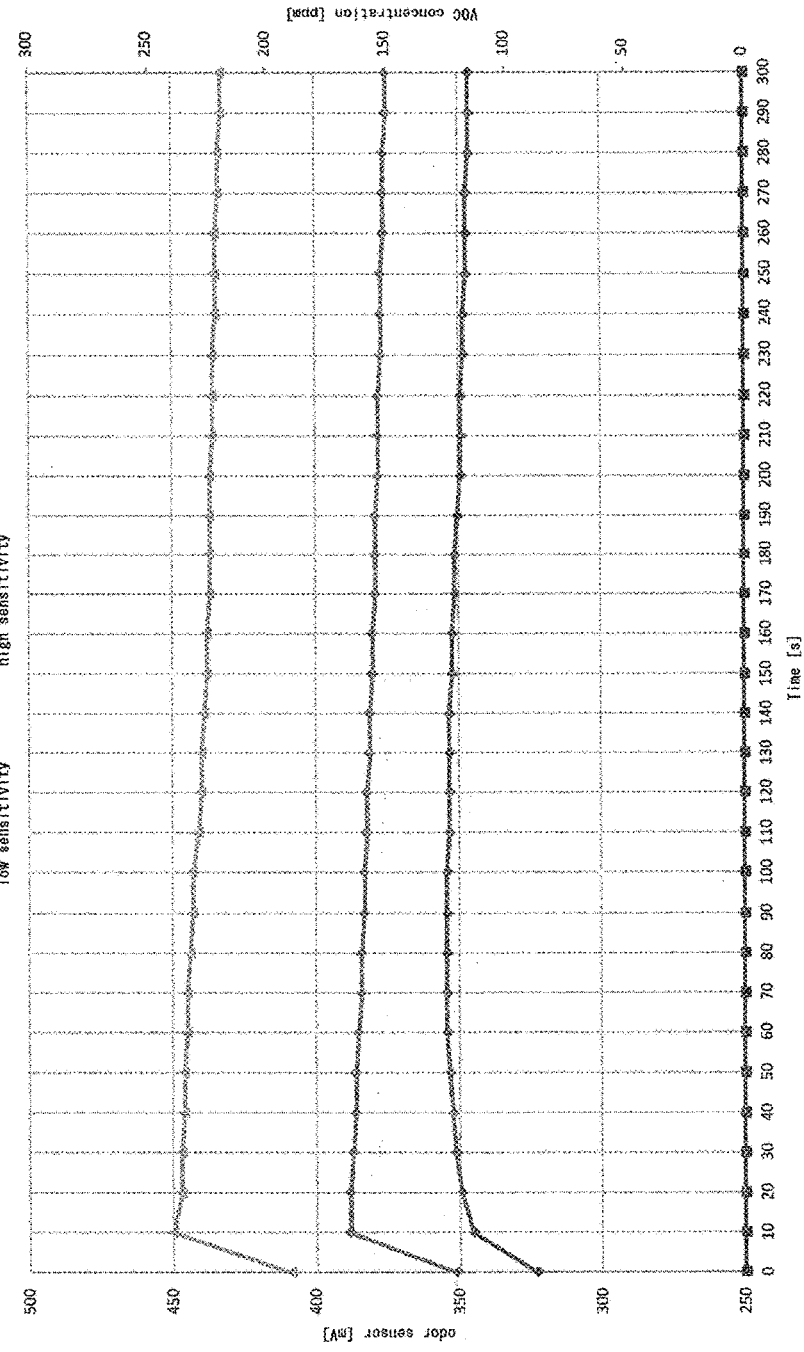
FIG. 33 shows results of odor sensor tests (Table 20)
Figure 34:
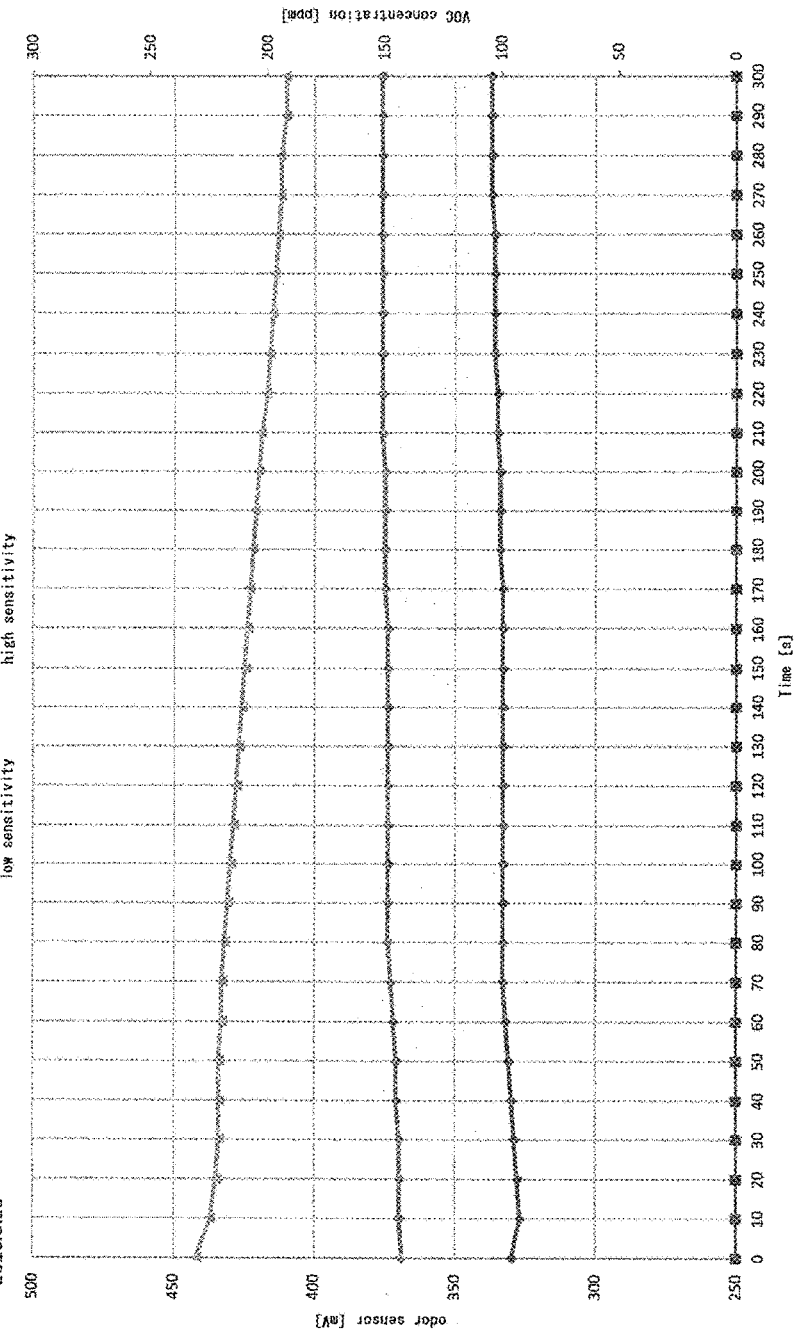
FIG. 34 shows results of odor sensor tests (Table 21)

FIG. 21 (Table 8) shows a graph of the measured values of Table 7 shown in FIG. 20.

It can be perceived that the higher the water temperature is, the higher the sensing performance of the odor sensor increases.

Next, FIG. 22 (Table 9) is a measurement table whose sensitivity has been made to be the highest by means of both the sensitivity-adjusting variable resistor 2a and the sensitivity range-adjusting knob 2b of the odor sensor control unit 2.

Immediately after the beginning and water temperature has been the least of 5 [Centigrade], the value measured by the odor sensor has been 343 [mV]. And, when the water temperature has been the most of 35 [Centigrade], the value measured by the odor sensor has been 393 [mV].

After 300 [s] from the beginning and the water temperature has been the least of 5 [Centigrade], the value measured by the odor sensor has been 468 [mV]. And, when the water temperature has been the most of 35 [Centigrade], the value measured by the odor sensor has been 640 [mV].

In comparison the low sensitivity setting of Table 7 with the high sensitivity setting of Table 8, it is clear that sensitivity-adjusting functions by means of both the sensitivity-adjusting variable resistor 2a and the sensitivity range-adjusting knob 2b of the odor sensor control unit 2 normally operate.

In the sensing tests, the following specification has been adapted to conduct tests related thereto.

Oily odors have been four kinds of: kerosene; light oil; gasoline; and engine oil.

Mold-odor substances have been geosmin and 2-MIB (2-methyliso borneol).

Test concentration has been 120 [mg/L] (only an oily odor), 60 [mg/L] (only an oily odor). 30 [mg/L] (only an oily odor), 15 [mg/L] (an oily odor and a mold odor), 5 [mg/L] (an oily odor and a mold odor), 1 [mg/L] (an oily odor and a mold odor), 0.25 [mg/L] (an oily odor and a mold odor), 0.01 [mg/L] (an oily odor and a mold odor), and 0.00001 [mg/L] (an oily odor and a mold odor).

Water temperature comparison has been performed at 5 [Centigrade], 10 [Centigrade], 15 [Centigrade], 20 [Centigrade], 25 [Centigrade], and 30 [Centigrade].

Sensitivity tests have been performed using "low sensitivity", "intermediate sensitivity", and "high sensitivity".

Natural tests using only pure water have been performed according to the same specification as the above.

In all of these tests, pleasant results have been obtained. In the following Embodiments, the specification is limited to as follows, and the sensing tests will now be shown with a graph related thereto.

Oily odors have been four kinds of: kerosene; light oil; gasoline; and engine oil. Mold-odor substances have been geosmin and 2-MIB (2-methyliso borneol). Water temperature has been performed at 15 [Centigrade]. Sensitivity tests have been performed at three steps using "low sensitivity", "intermediate sensitivity", and "high sensitivity".

Test concentration has been using two samples of 0.01 [mg/L] and 0.00001 [mg/L].

Figure 5:
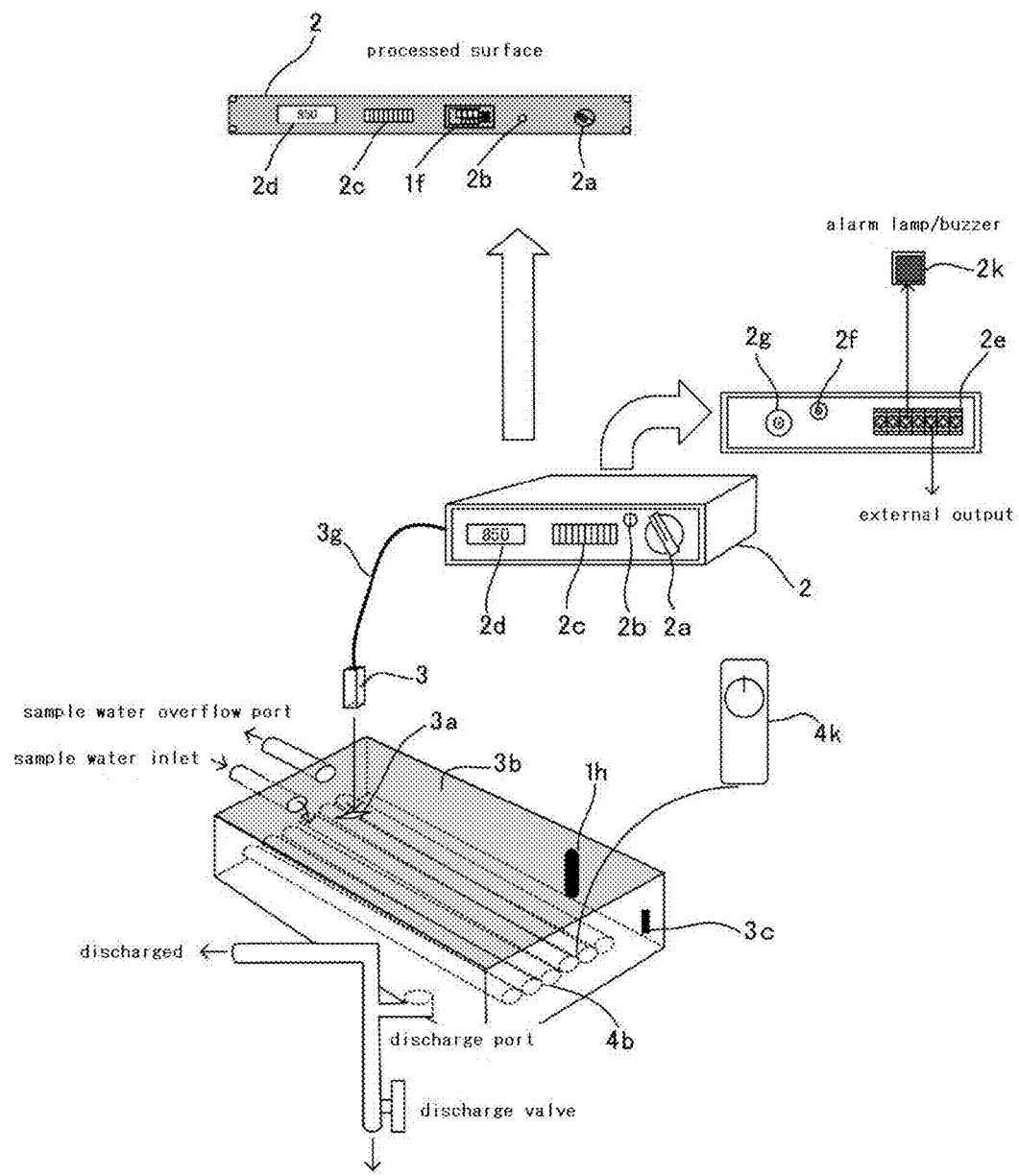
FIG. 5 is a block diagram showing an odor sensor control unit connected by a cable to an odor sensor sensing element provided in an odor-sensing water tank of the automatic water quality surveillance apparatus in Embodiment 2.

As shown in FIG. 5, the odor-sensing water tank's lid 3b is provided for the odor-sensing water tank 4a, and one portion of the lid is opened. The odor-sensing water tank 4a is inserted and fixed into the opened portion. Due to this, the tank can be easily filled with an odor to perform the sensing promptly.

The water inlet may be directly attached to the sensing tank 4a. In this case, the water level sensor 3c managing the water level is installed so as to prevent the heater from heating without water, and the temperature sensor 1h is installed so as to prevent a fire.

The odor-sensing water tank 4a should be stored within a cabinet or the like shut off from the open air. Due to this, an odor is prevented from being scattered to the periphery, and the tank can be protected from mixture of the odor and the open air. In other words, reaction by means of the object of such as an oily odor and a mold odor only can be made.

The odor sensor control unit 2 includes the sensitivity-adjusting variable resistor 2a of a rotary type that can be sifted from "low sensitivity" to "intermediate sensitivity", and from "intermediate sensitivity" to "high sensitivity" so as to perform six staged adjustment.

The sensitivity range-adjusting knob 2b adjusts a lower limit and an upper limit of the sensitivity-adjusting variable resistor 2a performing the six staged adjustment based on Table 22 (FIG. 35). Sensing can be performed according to each of the lower limit and the upper limit.

Utilizing the above-mentioned two items of the sensitivity-adjusting variable resistor and the sensitivity range-adjusting knob enables the followings. That is, erroneous sensing cause by the mixture of the odor and the open air other than oil contained within the raw water can be prevented. The sensing sensitivity can be adjusted to sense an oily odor and/or a mold odor optimally.

The upper line of Table 22 (FIG. 35) indicates the upper limit, and the lower line of the same indicates the lower limit. Using these lines, a range width is adjusted.

The upper line of Table 22 (FIG. 35) indicates the upper limit, and the lower line of the same indicates the lower limit. Using these lines, the range width can be adjusted.

Using a semiconductor sensor or the like measuring a change of an electric resistance caused by chemical absorption of reducible gas on a surface of a metal oxide semiconductor, the odor sensor sensing element 3 transmits output signals of the sensor to the odor sensor control unit 2 by means of the cable 3g.

All control such as digital processing of the signals of the semiconductor sensor, adjustment of the sensitivity, or the like is carried out by the microcomputer 2h.

Figure 9:
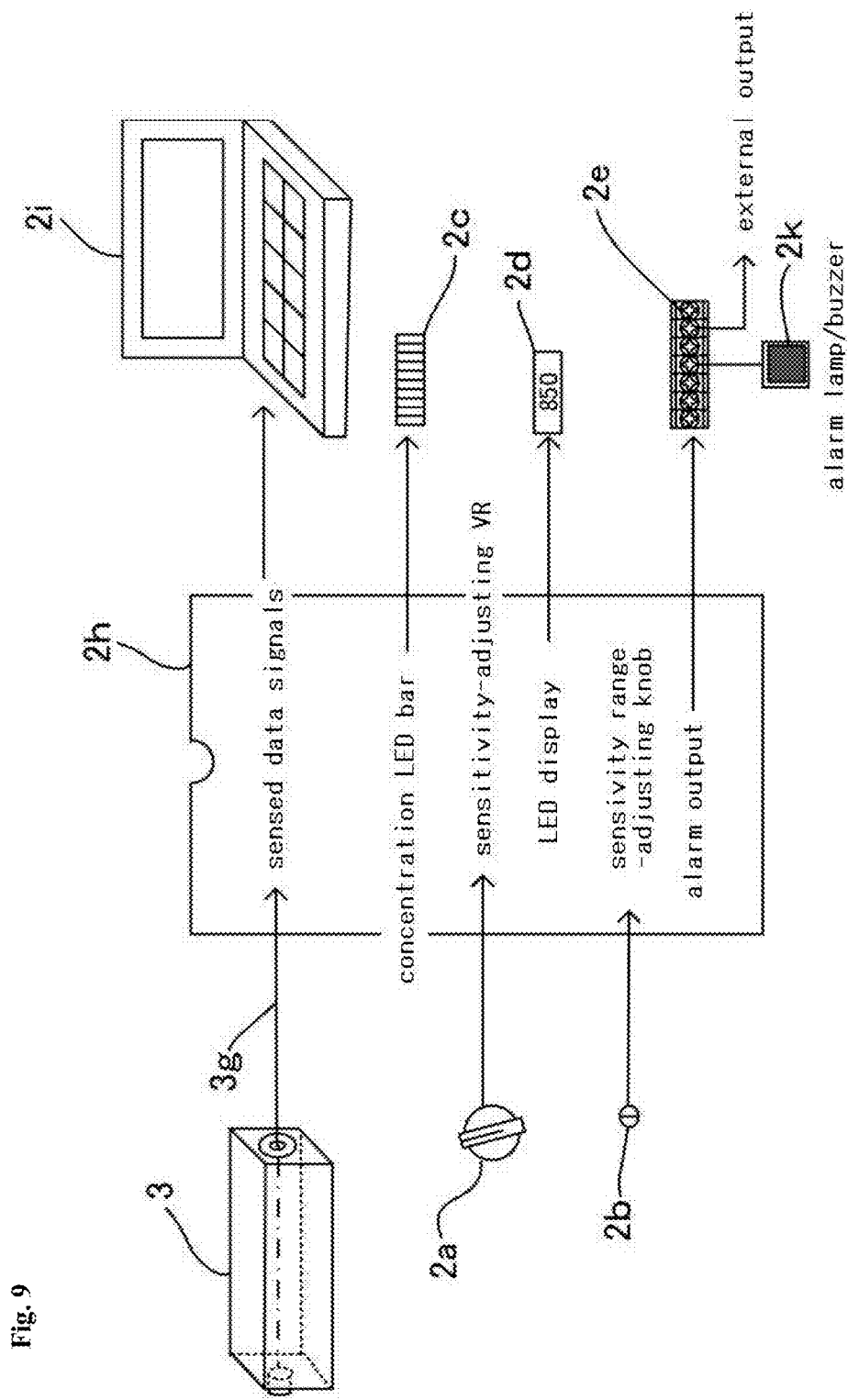
FIG. 9 is a block diagram showing input/output signals of a microcomputer implemented within the odor sensor control unit of the automatic water quality surveillance apparatus in any one of Embodiments 1 to 2.

As shown in FIG. 9, the signals of the semiconductor sensor provided with the odor sensor sensing element 3 is controlled by the microcomputer 2h within the odor sensor control unit 2 via the cable 3g.

The microcomputer 2h generates a conversion program for displaying the sensing data of the odor sensor sensing element 3 on the LCD display 2d.

The microcomputer also performs: switching the six staged sensitivity of the sensitivity-adjusting variable resistor 2a; and adjusting the range width of the upper limit and the lower limit related to the sensitivity range-adjusting knob 2b.

In addition, processing operation is performed upon sensing data by the odor sensor sensing element 3 to make the concentration LED bar 2c perform display fitting to the individual concentration.

The microcomputer is also provided with another program for outputting to the outside the sensing data of the odor sensor sensing element 3 reaching the sensitivity set up by the sensitivity-adjusting variable resistor 2a and the sensitivity range-adjusting knob 2b.

As shown in FIGS. 1 through 3 and FIGS. 6 through 9, the odor sensor sensing element 3 and the odor sensor control unit 2 are separately arranged and are connected to each other by means of the cable 3g.

The odor sensor sensing element 3 performs measurement continuously all day long in an inferior space where moisture and vapor generate. It is considered that the element may be more rapidly deteriorated than normal usage thereof.

It is enough that only the odor sensor sensing element 3 is exchanged. The apparatus according to the present invention can be reused by the less expensive component exchanging. The exchanging is easy and needs only a short time. Accordingly, there is a merit that shortening the working time leads to shortening the measurement time.

As shown in FIG. 3, the odor sensor control unit 2 may be of a panel type and/or a box type. When the panel type is juxtaposed to the display panel 1d of the automatic surveillance apparatus 1 with fish in FIG. 1, toxic substance surveillance and odor surveillance can be simultaneously performed to enable to make operation and surveillance easily, thereby eliminating overlooking, misread, and/or erroneous operation.

The box type has a merit that can be managed with simple work in a short time when the box type is going to be attached to the automatic surveillance apparatus with fish as an optional device.

The odor sensor control unit 2 is equipped with the sensitivity-adjusting variable resistor 2a and the sensitivity range-adjusting knob 2b. Due to this, sensitivity regarding an oily odor and a mold odor and kinds of an oily odor or a mold odor can be selected, and false reports can be eliminated.

The concentration LED bar 2c and the LED display 2d display odor concentration sensed by the odor sensor sensing element 3. Due to this, operating functions of the odor sensor sensing element 3 can be checked with eyes.

Figure 8:
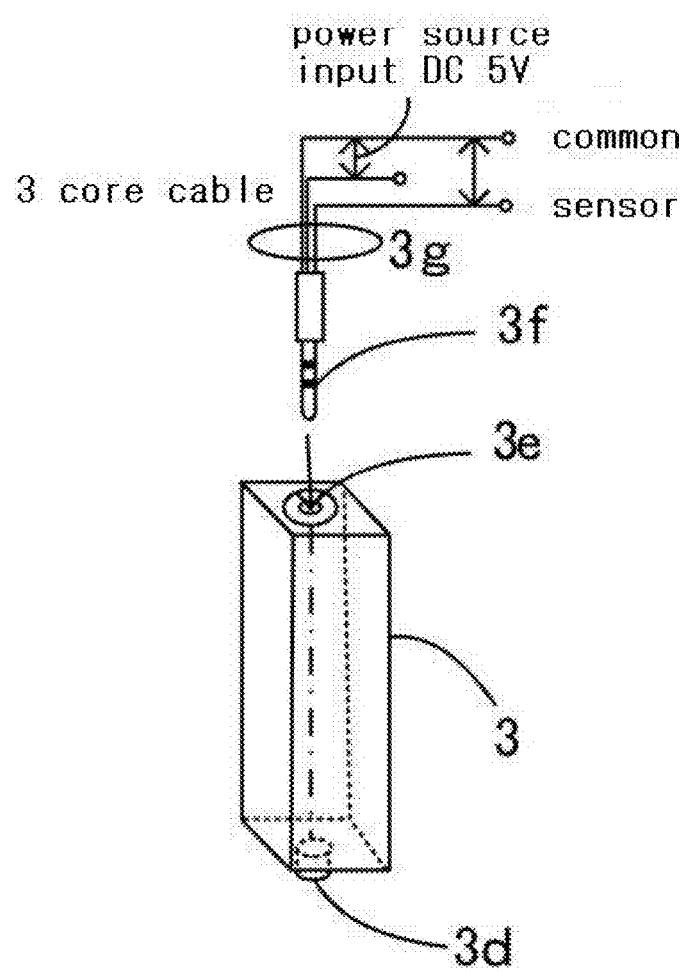
FIG. 8 is a connection diagram wherein a mini plug and a jack are inserted into the odor sensor sensing element with the cable of the automatic water quality surveillance apparatus in any one of Embodiments 1 to 2 to be connected to the cable.

As shown in FIG. 8, the odor sensor control unit 2 analyzes an oily odor, a mold odor, or the like sensed by the odor sensor sensing element 3. And, when alarm conditions are fulfilled, signals are automatically outputted to an alarm lamp, a buzzer and/or the outside.

In the odor sensor sensing element 3, like the portable VOC (Volatile Organic Compounds) monitor (Name: "Toxira Pro PID," produced by RAESYSTEMS (U.S.A.)) used as the evaluation device at this time, the monitor using a semiconductor sensor measuring a change of an electric resistance caused by chemical absorption of reducible gas on a surface of a metal oxide semiconductor, the odor sensor is normally configured by integrating the semiconductor sensor with a control unit thereof.

As shown in FIG. 3 and FIG. 5, this Embodiment is characterized by a separate type that signals outputted from the odor sensor sensing element 3 are transmitted to the odor sensor control unit 2 by means of the cable 3g as the sensing data.

The odor sensor sensing element 3 is installed at an upper portion of the heater 4b to make an oily odor and/or a mold odor stronger, thereby performing the sensing more easily.

This heater 4b has a role of preventing the fish from becoming suspended animation and/or stopping behavior thereof caused by water temperature drop.

As shown in FIG. 8, the odor sensor sensing element 3 and the odor sensor control unit 2 are separated from each other. The odor sensor sensing element 3, which is installed at an upper portion of the odor-sensing water tank 4a, is heated by the heater 4b to make the sensing easier. However, the odor sensor sensing element 3 is rapidly deteriorated cause by vapor and/or moisture.

Exchanging only the odor sensor sensing element 3 enables to provide a merit that the maintenance work thereof is less expensive and easy.

In the sensing odor sensor control unit 3, the sensitivity is well-adjusted by means of the sensitivity-adjusting variable resistor 2a and the sensitivity range-adjusting knob 2b. The concentration of an odor is numerically displayed on the concentration LED bar 2c and/or the LED display 2d. Herein, it is the alarm output terminal 2e of the reverse side of the odor sensor control unit 2 in FIG. 3 that, upon inflow of an oily odor and/or a mold odor, automatically senses it to output an alarm to the outside.

Figure 7:
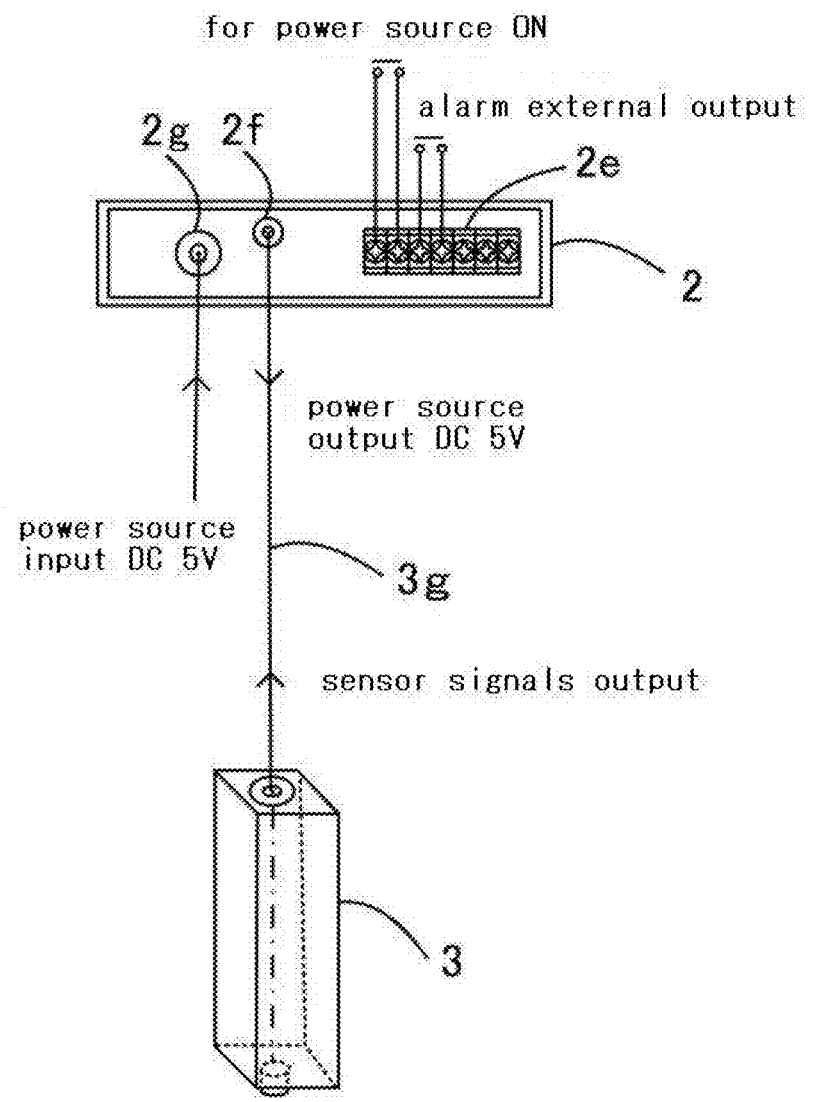
FIG. 7 is a connection diagram of a reverse side of the odor sensor control unit connected by the cable to the odor sensor sensing element of the automatic water quality surveillance apparatus in any one of Embodiments 1 to 2.

As shown in FIG. 7 and FIG. 8, the power source of the odor sensor sensing element 3 supplies output power DC 5 [V] thereof from the plug terminal 2f of the reverse side of the odor sensor control unit 2 via the cable 3g. And, the odor sensing data of the semiconductor device is sent to the microcomputer 2h from the plug terminal 2f of the reverse side of the odor sensor control unit 2 via the same cable 3g.

The sensing element of the odor sensor sensing element 3 uses the semiconductor sensor measuring a change of an electric resistance caused by chemical absorption of reducible gas on a surface of a metal oxide semiconductor, and transmits signals by means of the odor sensor sensing element 3.

As shown in FIG. 9, the odor sensing data signals generated by the semiconductor device of the odor sensor sensing element 3 are transmitted to the microcomputer 2h via the cable 3g. The microcomputer 2h of the odor sensor control unit 2 performs A/D conversion onto the transmitted odor sensing data signals to convert into the sensing data composed of digital vales from 0 to 1023. The digital values are displayed with level bars of the concentration LED bar 2c and/or are numerically displayed on the LED display 2d.

And, using the interrupt function of the microcomputer 2h, an alarm is outputted to the outside.

The microcomputer 2h generates:
a conversion program for displaying the sensing data signals from the element on the LED display 2d;
and another program for:
displaying on the concentration LED bar 2c data according to the six staged calculation onto the sensing data by means of the sensitivity-adjusting variable resistor 2a;
setting up alarm levels; and
an alarm-outputting circuit using the interrupt function of the microcomputer 2h.

In the odor sensor control unit 2, the sensitivity is switched in the six staged manner by means of the sensitivity-adjusting variable resistor 2a, and the range width is adjusted using the sensitivity range-adjusting knob 2b. In this way, an optimal value for an oily odor and/or a mold odor is selected.

Regarding the sensing precision of the odor sensor mentioned in the Embodiment according to the present invention, sensing tests have been made by means of the test device configuration shown in FIG. 6. As a result, sensing performance has been proved as shown in Table 7 through Table 22 (FIGS. 20-35).

As shown in FIG. 3, in the device configuration according to the present invention, the heater 4b (two 300 [w] ceramic heaters) is installed at the bottom portion of the odor-sensing water tank 4a.

And, the thermostat 4k connected to the heater 4b always keeps water temperature (e.g. within about 15 through 20 [Centigrade]) that small organisms such as cyprinodonts like.

For maintaining the sensing precision of the odor sensor and practical use, it is necessary to manage the water temperature within about 15 through 20 [Centigrade].

If the water temperature is not grater that 5 [Centigrade], the small organisms 4e such as cyprinodonts do not well move, and then stop moving. In this case, in the analysis of image processing, it may be erroneously judged that the organisms died caused by contamination by toxic substances, resulting in issuing a false alarm.

According to the present invention, the heater 4b is installed at the odor-sensing water tank 4a of the surveillance water tank 4 in the middle of the channel so as to keep the optimal water temperature for the small organisms 4e such as cyprinodonts within the water tank for fish 4d, while warming water temperature of the odor-sensing water tank 4a. Due to this, the following benefits can be obtained. That is, even if oil is less, dissolution gas derived from the oil together with vapor storms out, thereby increasing the sensitivity of the odor sensor sensing element 3.

Next, Embodiment 2 will now be described.

In explanation of Embodiment 2, explanation with respect to components as the same as those of Embodiment 1 is omitted, and only differences therefrom will be explained.

Embodiment 2

Referring to FIGS. 4 through 9, an automatic water quality surveillance apparatus in Embodiment 2 will now be explained.

Figure 4:
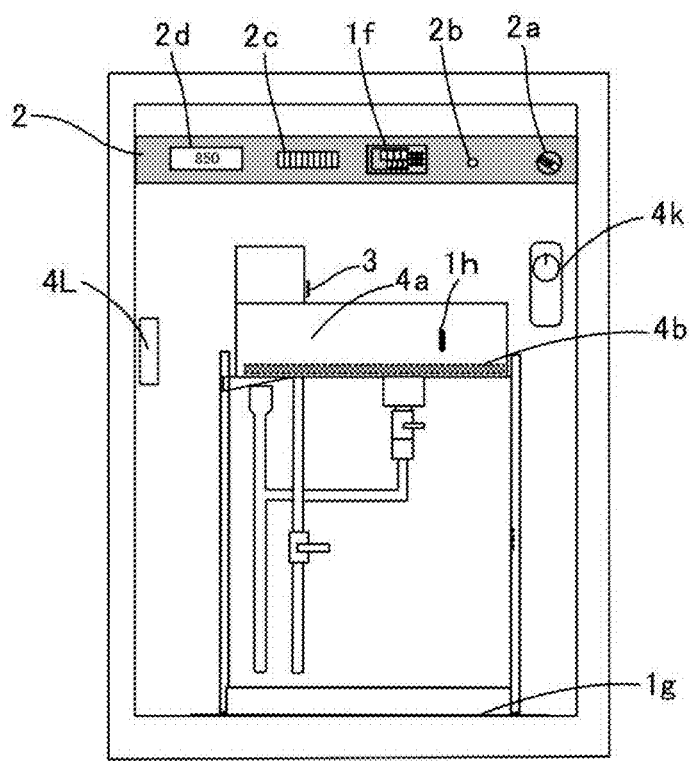
FIG. 4 is an outline view showing an automatic water quality surveillance apparatus in Embodiment 2.

Dissimilar to the automatic water quality surveillance apparatus with fish in Embodiment 1 whose odor sensor has been implemented therein, the automatic water quality surveillance apparatus with fish in Embodiment 2 is configured by only an odor sensor independent from the automatic water quality surveillance apparatus with fish. As shown in FIG. 4, the odor sensor is stored in a small storing case.

In FIG. 4, a symbol of "4b" indicates the heater, a symbol of "2" indicates the odor sensor control unit, a symbol of "4a" indicates the odor-sensing water tank, a symbol of "3" indicates the odor sensor sensing element, a symbol of "1f" indicates the water thermometer, a symbol of "4f" indicates the ventilation fan, and a symbol of "1g" indicates the leakage sensor, respectively.

According to the automatic water quality surveillance apparatus in Embodiment 2, as the same as the Embodiment 1, effect can be obtained, the effect enabling to sense inflow of oil and/or mold contained in the raw water.

In the above, Embodiments have been explained. Needless to say, the present invention is not limited to Embodiments, but also includes modification and/or variation therefrom within the scope of the present invention.

INDUSTRIAL APPLICABILITY

According to the present invention, the odor sensor capable of sensing an oily odor and/or a mold odor is provided for the automatic water quality surveillance apparatus with fish according to the bioassay method of sensing contamination to raw water (e.g. river flowing water, lake water, ground water, and so on.). With this structure, almost all of the water pollution accidents are prevented to contribute both the safety of water and comfortable food life.

So, the present invention is widely applicable for industrial fields including: water supply utilities; drink makers; food makers; and fields relevant to water of waste water, waste industrial water, and so on other than city water.

BRIEF DESCRIPTION OF SYMBOLS

1: Automatic water quality surveillance apparatus
1$a$: CCD video camera
1$b$: Image processing device
1$c$: Peripheral control unit
1$d$: Display panel
1$e$: Monitor television
1$f$: Water thermometer
1$g$: Water leakage sensor
1$h$: Temperature sensor
2: Odor sensor control unit
2$a$: Sensitivity-adjusting variable resistor
2$b$: Sensitivity range-adjusting knob
2$c$: Concentration LED bar
2$d$: LED display
2$e$: Terminal table
2$f$: Plug terminal
2$g$: DC power source plug
2$h$: Microcomputer
2$i$: Personal computer
2$j$: Portable VOC monitor
2$k$: Warning device
3: Odor sensor sensing element
3$a$: Element-mounting port
3$b$: Odor-sensing water tank's lid
3$c$: Water level sensor
3$d$: Element
3$e$: Connecting plug
3$f$: Connection jack
3$g$: Cable
4: Surveillance water tank
4$a$: Odor-sensing water tank
4$b$: Heater
4$c$: Underwater pump
4$d$: Water tank for fish
4$e$: Small organism
4$f$: Capture net
4$g$: Fluorescent lamp
4$h$: Solenoid valve
4$i$: Water-sampling container
4$j$: Feeder
4$k$: Thermostat
4$l$: Ventilation fan
4$m$: Water-receiving tank
4$n$: Water inlet
4$o$: Supply hole
4$p$: Water-receiving tank's overflow pipe
4$q$: Water tank for fish's overflow pipe
4$r$: Water level-adjusting pipe
4$s$: Drain port
4$t$: Semicircle board The entire disclosure of Japanese Patent Application No. 2016-179079 filed on Sep. 14, 2016 including specification, claims, drawings and summary is incorporated herein by reference in its entirety.

What is claimed is:

1. An automatic water quality surveillance apparatus, comprising:
a water tank for fish always and continuously receiving raw water so as to rear a plurality of cyprinodonts therein, the raw water including: river flowing water; lake water; and ground water; and
a CCD video camera photographing abnormal behavior when the raw water contains toxic substances therein, the abnormal behavior including:
a first case where the plurality of cyprinodonts form a fixed group that does not move;
a second case where the plurality of cyprinodonts take at least one of repelling action and madly-rushing action; and
a third case where the plurality of cyprinodonts die, wherein:
the automatic water quality surveillance apparatus performs digital conversion on image signals from the CCD video camera, and judges an abnormality according to image processing to automatically output an alarm;
the automatic water quality surveillance apparatus further comprising:
an odor-sensing water tank through which the raw water circulates;
an odor sensor sensing a mold odor of the odor-sensing water tank; and
a heater warming the raw water circulating within the odor-sensing water tank;
the odor sensor includes: an odor sensor sensing element; and an odor sensor control unit;
the odor sensor sensing element and the odor sensor control unit are separately arranged and are connected to each other by means of a cable;
the odor sensor sensing element is arranged within the odor-sensing water tank;
the odor sensor control unit includes:
a sensitivity-adjusting variable resistor adjusting an odor sensitivity; and
a sensitivity range-adjusting knob;
the automatic water quality surveillance apparatus further comprising:
an LED display displaying a level of odor concentration that the odor sensor sensing element is sensing; and
a concentration LED bar numerically displaying the odor concentration;
the odor-sensing water tank is isolated from open air except an inlet and outlet of the raw water, and signals from the odor sensor sensing element are controlled by means of a microcomputer implemented within the odor sensor control unit via the cable;
the microcomputer is configured for:
generating a conversion program for displaying sensing data sensed by the odor sensor sensing element on the LED display; and
making the concentration LED bar perform display according to the concentration obtained by stepped processing operation on the sensing data using the sensitivity-adjusting variable resistor of a rotary type;

the odor-sensing water tank is provided in a channel at a side of the water tank for fish receiving the raw water toward the water tank for fish that rears the fish;

a semiconductor sensor measuring a change of electric resistance caused by chemical absorption of reducible gas existing on a surface of a metal oxide semiconductor is utilized as the odor sensor sensing element; and the odor sensor control unit is juxtaposed to the display panel of the automatic water quality surveillance apparatus.

2. The automatic water quality surveillance apparatus as defined in claim 1, further comprising:

a thermostat automatically ON/OFF switching a power source of the heater, thereby controlling temperature of the raw water within the odor-sensing water tank;

a temperature sensor measuring the temperature of the raw water within the odor-sensing water tank; and a thermometer displaying the temperature of the raw water.

3. The automatic water quality surveillance apparatus as defined in claim 2, wherein the heater is composed of a ceramic heater.

4. The automatic water quality surveillance apparatus as defined in claim 2, wherein:

if the odor sensor sensing element senses a mold odor, the odor sensor control unit performs analysis thereof; and the automatic water quality surveillance apparatus further comprises an alarming device automatically outputting an alarm to the outside when alarming conditions are fulfilled.

5. The automatic water quality surveillance apparatus as defined in claim 1, wherein the heater is composed of a ceramic heater.

6. The automatic water quality surveillance apparatus as defined in claim 5, wherein:

if the odor sensor sensing element senses a mold odor, the odor sensor control unit performs analysis thereof; and the automatic water quality surveillance apparatus further comprises an alarming device automatically outputting an alarm to the outside when alarming conditions are fulfilled.

7. The automatic water quality surveillance apparatus as defined in claim 1, wherein:

if the odor sensor sensing element senses a mold odor, the odor sensor control unit performs analysis thereof; and the automatic water quality surveillance apparatus further comprises an alarming device automatically outputting an alarm to the outside when alarming conditions are fulfilled.

* * * * *